US006380463B1

(12) United States Patent
Jepson

(10) Patent No.: US 6,380,463 B1
(45) Date of Patent: Apr. 30, 2002

(54) INDUCIBLE HERBICIDE RESISTANCE

(75) Inventor: Ian Jepson, Maidenhead (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/011,151

(22) PCT Filed: Aug. 2, 1996

(86) PCT No.: PCT/GB96/01883

§ 371 Date: Jan. 29, 1998

§ 102(e) Date: Jan. 29, 1998

(87) PCT Pub. No.: WO97/06269

PCT Pub. Date: Feb. 20, 1997

(30) Foreign Application Priority Data

Mar. 8, 1995 (GB) .............................................. 9515941

(51) Int. Cl.$^7$ ........................ C12N 15/82; C12N 15/10; C12N 5/04; A01H 5/00; A01H 4/00

(52) U.S. Cl. ..................... 800/287; 435/69.1; 435/70.1; 435/71.1; 435/468; 435/410; 435/419; 435/418; 800/288; 800/300; 800/320; 800/278

(58) Field of Search ............................... 435/69.1, 70.1, 435/71.1, 468, 410, 419, 418; 800/287, 288, 300, 320, 278, 270

(56) References Cited

U.S. PATENT DOCUMENTS

| 5,198,345 A | 3/1993 | Gwynne et al. | ............ 435/69.1 |
|---|---|---|---|
| 5,503,991 A | 4/1996 | Gwynne et al. | ............ 435/69.1 |
| 5,728,547 A | 3/1998 | Gwynne et al. | ............ 435/69.1 |

FOREIGN PATENT DOCUMENTS

| EP | A-0332104 | 3/1989 |
|---|---|---|
| EP | A-0388186 | 4/1990 |
| WO | WO 86/06097 | 10/1986 |
| WO | WO 90/13658 | 11/1990 |
| WO | WO92/00377 | * 1/1992 |
| WO | WO 92/00377 | 1/1992 |
| WO | WO 92/04449 | 3/1992 |
| WO | WO 93/01294 | 1/1993 |
| WO | WO 93/05164 | 3/1993 |
| WO | WO 93/21334 | 10/1993 |
| WO | WO 96/25505 | 7/1996 |

OTHER PUBLICATIONS

Park et al. Plant Journal. 1996. Feb. issue. vol. 9: 183–194, 1994.*
Napoli et al. The Plant Cell. 1989. vol. 2: 278–289, 1989.*
Klee et al. Molecular and General Genetics. 1987. Dec. issue. vol. 210: 437–442, 1987.*
Kumberg et al. J. Biological Chemistry. 1992. Oct. issue. vol. 267: 21146–21153, 1992.*

Fillati, JJ. et al., "Efficient transfer of a glyphosate tolerance gene into tomato using binary agrobacterium tumefaciens vector", Biotechnology, vol. 5, No. 7, pp. 726–730, XP002022728, 1987.

Aoyama et al., "Ectopic Expression of the Arabidopsis Transcriptional Activator Athb–1 Alters Leaf Cell Fate in Tobacco", The Plant Cell, vol. 7, pp. 1773–1785, 1995.

Gatz, Christiane, "Chemical inducible promoters in Transgenic plants", Current Opinion in Biotechnology, vol. 7, pp. 168–172, 1996.

Hershey et al., "Isolation and characterization of cDNA clones for RNA species induced by substituted benzenesulfonamides in corn", Plant Molecular Biology, vol. 17, pp. 679–690, 1991.

Pateman et al., "Regulation of alcohol dehydrogenase (ADH) and aldehyde dehydrogenase (AldDH) in *Aspergillus nidulans*", Proc. R. Soc. Lond., vol. B 217, pp. 243–264, 1983.

Roland, LJ. and Strommer, JN., "Anaerobic Treatment of Maize Roots Affects Transcription of Adhl and Transcript Stability", Molecular and Cellular Biology, vol. 6, No. 10, pp. 3368–3372, 1986.

Lockington et al., "Cloning and characterization of the ethanol utilization regulon in *Aspergillus nidulans*", Gene, vol. 33, pp. 137–149, 1985.

Edwards et al., "A simple and rapid method for the preparation of plant genomic DNA for PCR analysis", Nucleic Acids Research, vol. 19, No. 6, p. 1349, 1991.

Jepson et al., "A Rapid Procedure for the Construction of PCR cDNA Libraries from Small Amounts of Plant Tissue", Plant Molecular Biology Reporter, vol. 9, pp. 131–138, 1991.

Rubin et al., "Glyphosate Inhibition of 5–Enolpyruvylshikimate 3–P–hosphate Synthase from Suspension–Cultured Cells of *Nicotiana silvestris*", Plant Physiol. vol. 75, pp. 839–845, 1984.

Mousdale, DM. and Coggins, JR "Purifiaction and properties of 5–enolpyruvylshikimate 3–phosphate synthase from seedlings of *Pisum sativum L.*", Planta, vol. 160, pp. 78–83. 1984.

Della–Cioppa et al., "Translocation of the precursor of 5–enolpyruvylshikimate 3–phosphate synthase into chloroplasts of higher plant in vitro", Proc. Natl. Acad. Sci.(USA), vol. 83, pp. 6873–6877, 1986.

(List continued on next page.)

*Primary Examiner*—Amy J. Nelson
*Assistant Examiner*—O. M. F. Zaghmout
(74) *Attorney, Agent, or Firm*—Hale and Dorr LLP

(57) ABSTRACT

The invention relates to DNA constructs which are capable of conferring on a plant inducible resistance to a herbicide. The inducible effect may be achieved by using a gene switch such as the alcA/alcR switch derived from *A. nidulans*. The invention relates in particular to inducible resistance to the herbicide N-phosphonomethyl glycine (glyphosate) and its salts.

20 Claims, 30 Drawing Sheets

OTHER PUBLICATIONS

Creaser et al., "Purification and preliminary characterization of alcohol dehydrogenase form *Aspergillus nidulans*", Biochemical J., vol. 225, pp. 449–454, 1985.

Felenbok et al., "The ethanol regulon in *Aspergillus nidulans*: characterization and sequence of the positive regualtory gene alcR", Gene, vol. 73, pp. 385–396, 1988.

Kulmburg et al., "Identification of the Promoter Region Involved in the Autoregulation of the Transcriptual Activator ALCR in *Aspergillus nidulans*", Molecular and Cellular Biology, vol. 12, No. 5, pp. 1932–1939, May 1992.

Bailey, C. and Arst, HN., "Carbon Catobolite Repression in *Aspergillus nidulans*", Eur. J. Biochem., vol. 51, pp. 573–577, 1975.

Pan, T. and Coleman, JE., "The DNA Binding Bomain of GAL4 Forms a Binuclear Metal Ion Complex", Biochemistry, vol. 29, pp. 3023–3029, 1990.

Halvorsen et al., "LAC9 DNA–binding Domain Coordinates Two Zinc Atoms Per Monomer and Contacts DNA as Dimer", The Journal of Biological Chemistry, vol. 265, No. 22, pp. 13283–13289, 1990.

Gwynne et al., "Comparison of the cis–acting control regions of two coordinately controlled genes involved in ethanol utilization in *Aspergillus nidulans*", Gene, vol. 51, pp. 205–216, 1987.

Pickett et al., "Cloning and charcterization of the aldA gene of *Apergillus nidulans*", Gene, vol. 51, pp. 217–226, 1987.

* cited by examiner

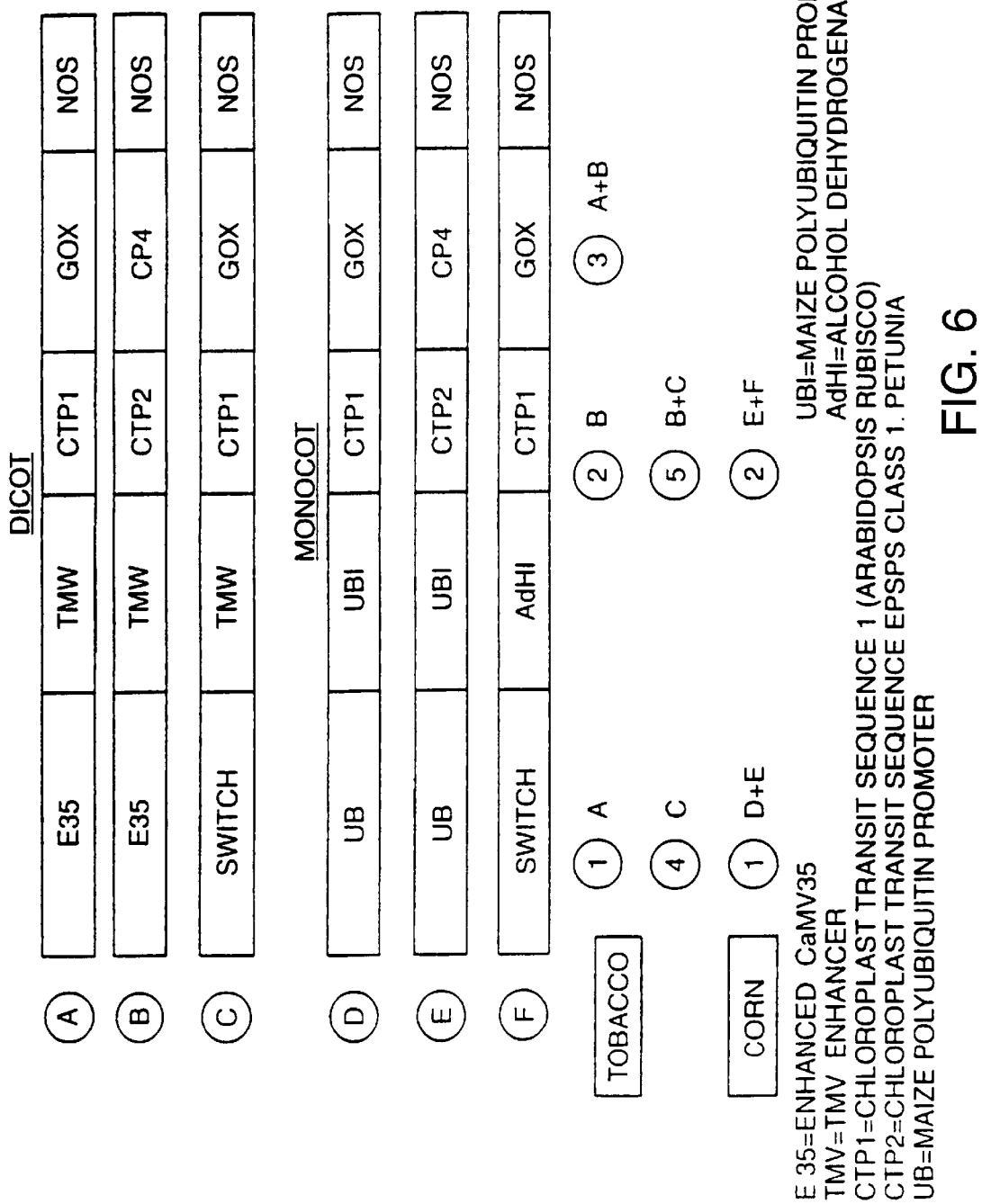

```
          10         20         30         40         50
    1234567890 1234567890 1234567890 1234567890 1234567890
    AAGCTTACCA TGGCTTCCTC TATGCTCTCT TCCGCTACTA TGGTTGCCTC    50
     K  L  T   M  A  S  S   M  L  S   S  A  T   M  V  A  S

TCCGGCTCAG GCCACTATGG TCGCTCCTTT CAACGGACTT AAGTCCTCCG   100
     P  A  Q   A  T  M  V   A  P  F   N  G  L   K  S  S  A

CTGCCTTCCC AGCCACCCGC AAGGCTAACA ACGACATTAC TTCCATCACA   150
     A  F  P   A  T  R   K  A  N  N   D  I  T   S  I  T

AGCAACGGCG AAGAGTTAA CTGTATGCAG GTGTGGCCTC CGATTGGAAA    200
     S  N  G  G   R  V  N   C  M  Q   V  W  P  P   I  G  K

GAAGAAGTTT GAGACTCTCT CTTACCTTCC TGACCTTACC GATTCCGGTG   250
     K  K  F   E  T  L  S   Y  L  P   D  L  T   D  S  G  G

GTCGCGTCAA CTGTATGCAG GCTATGGCTG AGAACCACAA GAAGGTTGGT   300
     R  V  N   C  M  Q   A  M  A   E  N  H  K   K  V  G

ATCGCTGGAG CTGGAATCGT TGGTGTTTGC ACTGCTTTGA TGCTTCAACG   350
     I  A  G  A   G  I  V   G  V  C   T  A  L  M   L  Q  R

TCGTGGATTC AAGGTTACCT TGATTGATCC AAACCCACCA GGTGAAGGTG   400
     R  G  F   K  V  T  L   I  D  P   N  P  P   G  E  G  A

CTTCTTTCGG TAACGCTGGT TGCTTCAACG GTTCCTCCGT TGTTCCAATG   450
     S  F  G   N  A  G   C  F  N  G   S  S  V   V  P  M

TCCATGCCAG GAAACTTGAC TAGCGTTCCA AAGTGGCTTC TGGATCCTGT   500
     S  M  P  G   N  L  T   S  V  P   K  W  L   L  D  P  V

TGTGAATTC                                                 509
     V  N
```

FIG. 7A

|  | 10 | 20 | 30 | 40 | 50 |  |
|---|---|---|---|---|---|---|
|  | 1234567890 | 1234567890 | 1234567890 | 1234567890 | 1234567890 |  |
|  | AAGCTTACGG | ATCCAATGGG | TCCATTGTCC | ATCCGTTTCA | GCTACTTTCC | 50 |
|  | K L T D | P M G | P L S | I R F S | Y F P |  |
|  | AACCATCATG | CCTTGGTTGA | TTCGTTTCTT | GCTTGCTGGA | AGACCAAACA | 100 |
|  | T I M | P W L I | R F L | L A G | R P N K |  |
|  | AGGTGAAGGA | GCAAGCTAAG | GCACTCCGTA | ACCTCATCAA | GTCCACTGTG | 150 |
|  | V K E | Q A K | A L R N | L I K | S T V |  |
|  | CCTTTGATCA | AGTCCTTGGC | TGAGGAGGCT | GATGCTAGCC | ACCTTATCCG | 200 |
|  | P L I K | S L A | E E A | D A S H | L I R |  |
|  | TCACGAAGGT | CACCTTACCG | TGTACCGTGG | AGAAGCAGAC | TTCGCCAAGG | 250 |
|  | H E G | H L T V | Y R G | E A D | F A K D |  |
|  | ACCGTGGAGG | TTGGGAACTT | CGTCGTCTCA | ACGGTGTTCG | TACTCAAATC | 300 |
|  | R G G | W E L | R R L N | G V R | T Q I |  |
|  | CTCAGCGCTG | ATGCATTGCG | TGATTTCGAT | CCTAACTTGT | CTCACGCCTT | 350 |
|  | L S A D | A L R | D F D | P N L S | H A F |  |
|  | TACCAAGGGA | ATCCTTATCG | AAGAGAACGG | TCACACCATC | AACCCACAAG | 400 |
|  | T K G | I L I E | E N G | H T I | N P Q G |  |
|  | GTCTCGTGAC | TCTCTTGTTT | CGTCGTTTCA | TCGCTAACGG | TGGAGAGTTC | 450 |
|  | L V T | L L F | R R F I | A N G | E F |  |
|  | GTGTCTGCTC | GTGTTATCGG | ATTCGAGACT | GAAGGTCGTG | CTCTCAAGGG | 500 |
|  | V S A R | V I G | F E T | E G R A | L K G |  |
|  | TATCACCACC | ACCAACGGTG | TTCTTGCTGT | TGATGCTGCA | GTGTTGTGAA | 550 |
|  | I T T | T N G V | L A V | D A A | V L . I |  |
|  | TTC |  |  |  |  | 553 |

FIG. 7B

```
              10          20          30          40          50
         1234567890  1234567890  1234567890  1234567890  1234567890
         AAGCTTACTG  CAGTTGTTGC  AGCTGGTGCA  CACTCCAAGT  CTCTTGCTAA   50
          K  L  T  A  V  V  A   A  G  A   H  S  K  S   L  A  N

CTCCCTTGGT  GATGACATCC  CATTGGATAC  CGAACGTGGA  TACCACATCG  100
          S  L  G   D  D  I  P   L  D  T   E  R  G   Y  H  I  V

TGATCGCCAA  CCCAGAAGCT  GCTCCACGTA  TTCCAACTAC  CGATGCTTCT  150
          I  A  N   P  E  A   A  P  R  I   P  T  T   D  A  S

GGAAAGTTCA  TCGCTACTCC  TATGGAGATG  GGTCTTCGTG  TTGCTGGAAC  200
          G  K  F  I   A  T  P   M  E  M   G  L  R  V   A  G  T

CGTTGAGTTC  GCTGGTCTCA  CTGCTGCTCC  TAACTGGAAG  CGTGCTCACG  250
          V  E  F   A  G  L  T   A  A  P   N  W  K   R  A  H  V

TTCTCTACAC  TCGTGCTCGT  AAGTTGCTTC  CAGCTCTCGC  TCCTGCCAGT  300
          L  Y  T   R  A  R   K  L  L  P   A  L  A   P  A  S

TCTGAAGAAC  GTTACTCCAA  GTGGATGGGT  TTCCGTCCAA  GCATCCCAGA  350
          S  E  E  R   Y  S  K   W  M  G   F  R  P  S   I  P  D

TTCCCTTCCA  GTGATTGGTC  GTGCTACCCG  TACTCCAGAC  GTTATCTACG  400
          S  L  P   V  I  G  R   A  T  R   T  P  D   V  I  Y  A

CTTTCGGTCA  CGGTCACCTC  GGTATGACTG  GTGCTCCAAT  GACCGCAACC  450
          F  G   H  G  H  L   G  M  T  G   A  P  M   T  A  T

CTCGTTTCTG  AGCTCCTCGC  AGGTGAGAAG  ACCTCTATCG  ACATCTCTCC  500
          L  V  S  E   L  L  A   G  E  K   T  S  I  D   I  S  P

ATTCGCACCA  AACCGTTTCG  GTATTGGTAA  GTCCAAGCAA  ACTGGTCCTG  550
          F  A  P   N  R  F  G   I  G  K   S  K  Q   T  G  P  A

CATCCTAAGG  TACCGAATTC                                      570
          S  .  G  T  E  F
```

| FIG. 8A |
|---|
| FIG. 8B |
| FIG. 8C |

```
              10          20          30          40          50          60
              |   SphI  PstI |         |→35S        |           |           |
        HindIII
  1   AAGCTT GCAT GCCTGCAGGT CAACATGGTG GAGCACGACA CACTTGTCTA CTCCAAAAAT  ⎫
      TTCGAA CGTA CGGACGTCCA GTTGTACCAC CTCGTGCTGT GTGAACAGAT GAGGTTTTTA  ⎪
                                                                          ⎪
 61   ATCAAAGATA CAGTCTCAGA AGACCAAAGG GCAATTGAGA CTTTTCAACA AAGGGTAATA   ⎪
      TAGTTTCTAT GTCAGAGTCT TCTGGTTTCC CGTTAACTCT GAAAAGTTGT TTCCCATTAT   ⎪
                                                                          ⎪  DUF
121   TCCTCGGATT GTGGCTCCTA CCATTGCCCA GCTATCTGTC ACTTTATTGT GAAGATAGTG   ⎬  ATC
      AGGAGCCTAA CACCGAGGAT GGTAACGGGT CGATAGACAG TGAAATAACA CTTCTATCAC   ⎪  EN
                                                                          ⎪
181   GAAAGGAAG GTGGCTCCTA CAAATGCCAT CATTGCGATA AAGGAAAGGC CATCGTTGAA   ⎪
      CTTTCCTTC CACCGAGGAT GTTTACGGTA GTAACGCTAT TTCCTTTCCG GTAGCAACTT   ⎪
                                                                          ⎪
241   GATGCCCTCTG CCGACAGTGG TCCCAAAGAT GGACCCCCAC CCACGAGGAG CATCGTTGAA  ⎪
      CTACGGGAGAC GGCTGTCACC AGGGTTTCTA CCTGGGGGTG GGTGCTCCTC GTAGCACCTT  ⎭
```

FIG. 8A

```
                                                                         ⎫
                                                                         ⎪ 35S
                                                                         ⎬ PR
                                                                         ⎪
                                                                         ⎭
                                                     ↓
301  AAAAGAAGAC  GTTCCAACCA  CGTCTTCAAA  GCAAGTGGAT  TGATGTGATA  ACATGGTGGA
     TTTTCTTCTG  CAAGGTTGGT  GCAGAAGTTT  CGTTCACCTA  ACTACACTAT  TGTACCACCT

361  GCACGACACA  CTTGTCTACT  CCAAAAATAT  CAAAGATACA  GTCTCAGAAG  ACCAAAGGGC
     CGTGCTGTGT  GAACAGATGA  GGTTTTTATA  GTTTCTATGT  CAGAGTCTTC  TGGTTTCCCG

421  AATTGAGACT  TTTCAACAAA  GGGTAATATC  CGGAAACCTC  ATTGCCCAGC  CTCGGATTCC
     TTAACTCTGA  AAAGTTGTTT  CCCATTATAG  GCCTTTGGAG  TAACGGGTCG  GAGCCTAAGG

481  TATCTGTCAC  TTTATTGTGA  AGATAGTGGA  AAAGGAAGGT  GGCTCCTACA  AATGCCATCA
     ATAGACAGTG  AAATAACACT  TCTATCACCT  TTTCCTTCCA  CCGAGGATGT  TTACGGTAGT

541  TTGCGATAAA  GGAAAGGCCA  TCGTTGAAGA  TGCCTCTGCC  GACAGTGGTC  CCAAAGATGG
     AACGCTATTT  CCTTTCCGGT  AGCAACTTCT  ACGGAGACGG  CTGTCACCAG  GGTTTCTACC

601  ACCCCCACCC  ACGAGGAGCA  TCGTGGAAAA  AAGAAGACGT  TCCAACCACG  TCTTCAAAGC
     TGGGGGTGGG  TGCTCCTCGT  AGCACCTTTT  TTCTTCTGCA  AGGTTGGTGC  AGAAGTTTCG

661  AAGTGGATTG  ATGT GATATC  TCCACTGACG  TAAGGGATGA  CGCACAATCC  CACTATCCTT
     TTCACCTAAC  TACA CTATAG  AGGTGACTGC  ATTCCCTACT  GCGTGTTAGG  GTGATAGGAA
                 EcoRV       ↑Promoter
```

FIG. 8B

```
                                                                    TM
                                                                    Ω
721  CGCAAGACCC TTCCTCTTATA TAAGGAAGTT CATTTCATTT GGAGAGGACC TCGAGTATTT
     GCGTTCTGGG AAGGAGATAT ATTCCTTCAA GTAAAGTAAA CCTCTCCTGG AGCTCATAAA
                 TATA BOX                              →TSP XhoI

781  TTACAACAAT TACCAACAAC AACAAACAAC AAACAACATT TTTACAATTA
     AATGTTGTTA ATGGTTGTTG TTGTTTGTTG TTTGTTGTAA AAATGTTAAT
                          SmaI

841  CACCATGGAT CCCCGGGTAC CGAGCTCGAA TTTCCCCGAT CGTTCAAACA TTTGGCAATA
     GTGGTACCTA GGGGCCCATG GCTCGAGCTT AAAGGGGCTA GCAAGTTTGT AAACCGTTAT
     NcoI         KpnI  SacI
         BamHI

901  AAGTTTCTTA AGATTGAATC CTGTTGCCGG TCTTGCGATG ATTATCATAT AATTTCTGTT
     TTCAAAGAAT TCTAACTTAG GACAACGGCC AGAACGCTAC TAATAGTATA TTAAAGACAA

961  GAATTACGTT AAGCATGTAA AATTATACAT GTAATGCATG ACGTTATTA TGAGATGGGT
     CTTAATGCAA TTCGTACATT TTAATATGTA CATTACGTAC TGCAATAAAT ACTCTACCCA

1021 TTTTATGATT AGAGTCCCGC AATTATACGC ATAGAAAACA AATATAGCG
     AAAATACTAA TCTCAGGGCG TTAATATGCG TATCTTTTGT TTTATATCGC

1081 CGCAAACTAG GATAAATTAT CGCGCCGCGT GTCATCTATG TTACTAGATC GGAATTC
     GCGTTTGATC CTATTTAATA GCGCGGCGCA CAGTAGATAC AATGATCTAG CCTTAAG
                                                          EcoRI
```

NOS
                                                                    3

Total number of bases is: 1138.
DNA sequence composition:    370 A;   253 C;   234 G;   281 T;   0 OTHER;

Sequence name: PMJB1

FIG. 8C

```
          10         20         30         40         50
    1234567890 1234567890 1234567890 1234567890 1234567890
    AAGCTTACCA TGGCTCAAGT TAGCAGAATC TGCAATGGTG TGCAGAACCC    50
      K  L  T   M  A  Q  V   S  R  I   C  N  G  V   Q  N  P

ATCTCTTATC TCCAATCTCT CGAAATCCAG TCAACGCAAA TCTCCCTTAT   100
      S  L  I   S  N  L  S   K  S  S   Q  R  K   S  P  L  S

CGGTTTCTCT GAAGACGCAG CAGCATCCAC GAGCTTATCC GATTTCGTCG   150
      V  S  L   K  T  Q   Q  H  P  R   A  Y  P   I  S  S

TCGTGGGGAT TGAAGAAGAG TGGGATGACG TTAATTGGCT CTGAGCTTCG   200
      S  W  G  L   K  K  S   G  M  T   L  I  G   S  E  L  R

TCCTCTTAAG GTCATGTCTT CTGTTTCCAC GGCGTGTATG CTTCACGGTG   250
      P  L  K   V  M  S  S   V  S  T   A  C  M   L  H  G  A

CAAGCAGCCG TCCAGCAACT GCTCGTAAGT CCTCTGGTCT TTCTGGAACC   300
      S  S  R   P  A  T   A  R  K  S   S  G  L   S  G  T

GTCCGTATTC CAGGTGACAA GTCTATCTCC CACAGGTCCT TCATGTTTGG   350
      V  R  I  P   G  D  K   S  I  S   H  R  S   F  M  F  G

AGGTCTCGCT AGCGGTGAAA CTCGTATCAC CGGTCTTTTG GAAGGTGAAG   400
      G  L  A   S  G  E  T   R  I  T   G  L  L   E  G  E  D

ATGTTATCAA CACTGGTAAG GCTATGCAAG CTATGGGTGC CAGGATCCTG   450
      V  I  N   T  G  K   A  M  Q  A   M  G  A   R  I  L

TTGTGAATTC                                               460
      L  .  I
```

FIG. 10A

```
          10         20         30         40         50
    1234567890 1234567890 1234567890 1234567890 1234567890
    AAGCTTAGGA TCCGTAAGGA AGGTGATACT TGGATCATTG ATGGTGTTGG    50
     K  L  R  I  R  K  E  G  D  T  W  I  I  D  G  V  G

TAACGGTGGA CTCCTTGCTC CTGAGGCTCC TCTCGATTTC GGTAACGCTG   100
     N  G  G  L  L  A  P  E  A  P  L  D  F  G  N  A  A

CAACTGGTTG CCGTTTGACT ATGGGTCTTG TTGGTGTTTA CGATTTCGAT   150
      T  G  C  R  L  T  M  G  L  V  G  V  Y  D  F  D

AGCACTTTCA TTGGTGACGC TTCTCTCACT AAGCGTCCAA TGGGTCGTGT   200
      S  T  F  I  G  D  A  S  L  T  K  R  P  M  G  R  V

GTTGAACCCA CTTCGCGAAA TGGGTGTGCA GGTGAAGTCT GAAGACGGTG   250
     L  N  P  L  R  E  M  G  V  Q  V  K  S  E  D  G  D

ATCGTCTTCC AGTTACCTTG CGTGGACCAA AGACTCCAAC GCCAATCACC   300
       R  L  P  V  T  L  R  G  P  K  T  P  T  P  I  T

TACAGGGTAC CTATGGCTTC CGCTCAAGTG AAGTCCGCTG TTCTGCTTGC   350
      Y  R  V  P  M  A  S  A  Q  V  K  S  A  V  L  L  A

TGGTCTCAAC ACCCCAGGTA TCACCACTGT TATCGAGCCA ATCATGACTC   400
      G  L  N  T  P  G  I  T  T  V  I  E  P  I  M  T  R

GTGACCACAC TGAAAAGATG CTTCAAGGTT TTGGTGCTAA CCTTACCGTT   450
      D  H  T  E  K  M  L  Q  G  F  G  A  N  L  T  V

GAGACTGATG CTGACGGTGT GCGTACCATC CGTCTTGAAG GTCGTGGTAA   500
     E  T  D  A  D  G  V  R  T  I  R  L  E  G  R  G  K

GCTCACCGGT CAAGTGATTG ATGTTCCAGG TGATCCATCC TCTACTGCTT   550
      L  T  G  Q  V  I  D  V  P  G  D  P  S  S  T  A  F

TCCCATTGGT TGCTGCCTTG CTTGTTCCAG GTTCGACGT CACCATCCTT    600
      P  L  V  A  A  L  L  V  P  G  S  D  V  T  I  L

AACGTTTTGA TGAACCCAAC CCGTACTGGT CTCATCTTGA CTCTGCAGTG   650
      N  V  L  M  N  P  T  R  T  G  L  I  L  T  L  Q  C
```

FIG. 10B

```
          10         20         30         40         50
 1234567890 1234567890 1234567890 1234567890 1234567890
TTGTGAATTC                                                    660
 C  E  F
```

FIG. 10C

```
          10         20         30         40         50
 1234567890 1234567890 1234567890 1234567890 1234567890
 AAGCTTCTGC AGGAAATGGG TGCCGACATC GAAGTGATCA ACCCACGTCT    50
  K  L  L  Q  E  M  G  A  D  I  E  V  I  N  P  R  L

TGCTGGTGGA GAAGACGTGG CTGACTTGCG TGTTCGTTCT TCTACTTTGA   100
  A  G  G  E  D  V  A  D  L  R  V  R  S  S  T  L  K

AGGGTGTTAC TGTTCCAGAA GACCGTGCTC CTTCTATGAT CGACGAGTAT   150
  G  V  T  V  P  E  D  R  A  P  S  M  I  D  E  Y

CCAATTCTCG CTGTTGCAGC TGCATTCGCT GAAGGTGCTA CCGTTATGAA   200
  P  I  L  A  V  A  A  A  F  A  E  G  A  T  V  M  N

CGGTTTGGAA GAACTCCGTG TTAAGGAAAG CGACCGTCTT TCTGCTGTCG   250
  G  L  E  E  L  R  V  K  E  S  D  R  L  S  A  V  A

CAAACGGTCT CAAGCTCAAC GGTGTTGATT GCGATGAAGG TGAGACTTCT   300
  N  G  L  K  L  N  G  V  D  C  D  E  G  E  T  S

CTCGTCGTGC GTGGTCGTCC TGACGGTAAG GGTCTCGGTA ACGCTTCTGG   350
  L  V  V  R  G  R  P  D  G  K  G  L  G  N  A  S  G

AGCAGCTGTC GCTACCCACC TCGATCACCG TATCGCTATG AGCTTCCTCG   400
  A  A  V  A  T  H  L  D  H  R  I  A  M  S  F  L  V

TTATGGGTCT CGTTTCTGAA AACCCTGTTA CTGTTGATGA TGCTACTATG   450
  M  G  L  V  S  E  N  P  V  T  V  D  D  A  T  M

ATCGCTACTA GCTTCCCAGA GTTCATGGAT TTGATGGCTG GTCTTGGAGC   500
  I  A  T  S  F  P  E  F  M  D  L  M  A  G  L  G  A

TAAGATCGAA CTCTCCGACA CTAAGGCTGC TTGATGAGCT CGAATTC      550
  K  I  E  L  S  D  T  K  A  A  .  .  A  R  I
```

FIG. 10D

Ubiquitin promoter fragment PCRed from maize.
2 Kb. fragment cloned into pUC19.
Junctions have been sequenced to confirm that it is the Ubiquitin promoter.

US 6,380,463 B1

INDUCIBLE HERBICIDE RESISTANCE

The present invention relates to DNA constructs and plants incorporating them. In particular it relates to promoter sequences for the expression of genes which confer herbicide resistance on plants.

Recent advances in plant biotechnology have resulted in the generation of transgenic plants resistant to herbicide application. Herbicide tolerance has been achieved using a range of different transgenic strategies. One well documented example is the use the bacterial xenobiotic detoxifying gene phosphinothricin acetyl transferase (PAT) from *Streptomyces hydroscopicus*. Mutated genes of plant origin, for example the altered target site gene encoding acetolactate synthase (ALS) from Arabidopsis, have been successfully utilised to generate transgenic plants resistant to herbicide application. The PAT and ALS genes have been expressed under the control of strong constitutive promoter.

We propose a system where genes conferring herbicide tolerance would be expressed in an inducible manner dependent upon application of a specific activating chemical. This approach has a number of benefits for the farmer, including the following:

1. Inducible control of herbicide tolerance would alleviate any risk of yield penalties associated with high levels of constitutive expression of herbicide resistance genes. This may be a particular problem as early stages of growth where high levels of transgene product may directly interfere with normal development. Alternatively high levels of expression of herbicide resistance genes may cause a metabolic drain for plant resources.
2. The expression of herbicide resistance genes in an inducible manner allows the herbicide in question to be used to control volunteers if the activating chemical is omitted during treatment.
3. The use of an inducible promoter to drive herbicide resistance genes will reduce the risk of resistant weed species becoming a major problem. If resistance genes were passed onto weed species from related crops, control could still be achieved with the herbicide in the absence of inducing chemical. This would particularly be relevant if the tolerance gene confirmed resistance to a total vegetative control herbicide which would be used (with no inducing chemical) prior to sowing the crop and potentially after the crop has been harvested. For example, it can be envisaged that herbicide resistance in cereals, such as wheat, might outcross into the weed wild oats or that herbicide resistance in oil seed rape or canola could be transferred to wild brassicas thus conferring herbicide resistance to these already troublesome weeds. A further example is that the inducible expression of herbicide resistance in sugar beet will reduce the risk of wild sugar beet becoming a problem.

Several gene regulation systems (gene switches) are known and may be used for conferring inducible herbicide resistance on plants. Many such gene switches are described in the review by Gatz (Current Opinion in Biotechnology (1996) 7, 168–172) and include systems such as the tetracycline repressor gene switch, the Lac repressor system, copper inducible systems such as that based on ACE 1, salicylic acid inducible promoters including the PR-1a system and systems based on steriodal hormones such as the glucocorticoid, progesterone and oestrogen receptor systems. Modifications of the glucocorticoid receptor systems which include the GAL 4 binding domain from yeast and the VP 16 activator are described by Aoyama et al, *The Plant Cell*, (1995) 7, 1773–1785 and it is envisaged that similar systems may based on, for example insect steroid hormones rather than on mammalian steriod hormones. Indeed, a system based on the ecdysone receptor of *Heliothis virescens* has recently been described. Benzene sulphonamide gene switching systems are also known (Hershey et al, *Plant Mol. Biol.*, 17, 679–690 (1991) as are systems based on the alcR protein from *Aspergillus nidulans* and glutathione S-transferase promoters.

Several genes which confer herbicide resistance are also known, for example, one herbicide to which resistance genes have been described and which is extremely widely used is N-phosphonomethyl-glycine (glyphosate) and its agriculturally acceptable salts including the isopropylamine, trimethylsulphonium, sodium, potassium and ammonium salts.

In a first aspect of the present invention there is provided a chemically inducible plant gene expression cassette comprising an inducible promoter operatively linked to a target gene which confers resistance to a herbicide.

Any herbicide resistance gene may be used but genes which confer resistance to N-phosphonomethyl-glycine or salts or derivatives thereof are especially preferred.

Several inducible promoters may be used to confer the inducible resistance and these include any of those listed above.

However, a particularly useful gene switch for use in this area is based on the alcR regulatory protein from *Aspergilluis nidulans* which activates genes expression from the alcA promoter in the presence of certain alcohols and ketones. This system is described in our International Patent Publication No. WO93/21334 which is incorporated herein by reference.

The alcA/alcR gene activation system from the fungus *Aspergillus nidulans* is also well characterised. The ethanol utilisation pathway in *A. nidulans* is responsible for the degradation of alcohols and aldehydes. Three genes have been shown to be involved in the ethanol utilisation pathway. Genes alcA and alcR have been shown to lie close together on linkage group VII and aldA maps to linkage group VIII (Pateman J H et al, 1984, Proc. Soc. Lond, B217:243–264; Sealy-Lewis E M and Lockington R A, 1984, Curr. Genet, 8:253–259). Gene alcA encodes ADHI in *A. nidulans* and aldA encodes aldDH, the second enzyme responsible for ethanol utilisation. The expression of both alcA and aldA are induced by ethanol and a number of other inducers (Creaser E H et al, 1984, Biochemical J. 255:449–454) via the transcription activator alcR. The alcR gene and a co-inducer are responsible for the expression of alcA and aldA since a number of mutations and deletions in alcR result in the pleiotropic loss of ADHI and aldDH (Felenbok B et al, 1988, Gene, 73:385–396; Pateman et al, 1984; Sealy-Lewis & Lockington, 1984). The ALCR protein activates expression from alcA by binding to three specific sites in the alcA promoter (Kulmberg P et al, 1992, J. Biol. Chem, 267:21146–21153).

The alcR gene was cloned (Lockington R A et al, 1985, Gene, 33:137–149) and sequenced (Felenbok et al, 1988). The expression of the alcR gene is inducible, autoregulated and subject to glucose repression mediated by the CREA repressor (Bailey C and Arst H N, 1975, Eur. J. Biochem, 51:573–577; Lockington R A et al, 1987, Mol. Microbiology, 1:275–281; Dowzer C E A and Kelly J M, 1989, Curr. Genet, 15:457–459; Dowzer C E A and Kelly J M, 1991, Mol. Cell. Biol, 11:5701–5709). The ALCR regulatory protein contains 6 cysteines near its N terminus coordinated in a zinc binuclear cluster (Kulmberg P et al, 1991, FEBS Letts, 280:11–16). This cluster is related to highly conserved DNA binding domains found in transcription factors of other ascomycetes. Transcription factors GAL4 and LAC9 have been shown to have binuclear complexes which have a cloverleaf type structure containing two Zn(II) atoms (Pan T and Coleman J E, 1990, Biochemistry, 29:3023–3029; Halvorsen Y D C et al, 1990, J. Biol. Chem, 265:13283–13289). The structure of ALCR is similar to this type except for the presence of an asymmetrical loop of 16 residues between Cys-3 and Cys-4. ALCR positively activates expression of itself by binding to two specific sites in its promoter region (Kulmberg P et al, 1992, Molec. Cell. Biol, 12:1932–1939).

The regulation of the three genes, alcR, alcA and aldA, involved in the ethanol utilisation pathway is at the level of transcription (Lockington et al, 1987; Gwynne D et al, 1987, Gene, 51:205–216; Pickett et al, 1987, Gene, 51:217–226).

There are two other alcohol dehydrogenases present in *A. nidulans*. ADHII is present in mycelia grown in non-induced media and is repressible by the presence of ethanol. ADHII is encoded by alcB and is also under the control of alcR (Sealy-Lewis & Lockington, 1984). A third alcohol dehydrogenase has also been cloned by complementation with a adh-strain of *S. cerevisiae*. This gene alcC, maps to linkage group VII but is unlinked to alcA and alcR. The gene, alcC, encodes ADHIII and utilises ethanol extremely weakly (McKnight G L et al, 1985, EMBO J, 4:2094–2099). ADHIII has been shown to be involved in the survival of *A. nidulans* during periods of anaerobic stress. The expression of alcC is not repressed by the presence of glucose, suggesting that it may not be under the control of alcR (Roland L J and Stromer J N, 1986, Mol. Cell. Biol, 6:3368–3372).

In summary, *A. nidulans* expresses the enzyme alcohol dehydrogenase I (ADH1) encoded by the gene alcA only when it is grown in the presence of various alcohols and ketones. The induction is relayed through a regulator protein encoded by the alcR gene and constitutively expressed. In the presence of inducer (alcohol or ketone), the regulator protein activates the expression of the alcA gene. The regulator protein also stimulates expression of itself in the presence of inducer. This means that high levels of the ADH1 enzyme are produced under inducing conditions (i.e. when alcohol or ketone are present). Conversely, the alcA gene and its product, ADH1, are not expressed in the absence of inducer. Expression of alcA and production of the enzyme is also repressed in the presence of glucose.

Thus the alcA gene promoter is an inducible promoter, activated by the alcR regulator protein in the presence of inducer (i.e. by the protein/alcohol or protein/ketone combination). The alcR and alcA genes (including the respective promoters) have been cloned and sequenced (Lockington R A et al, 1985, Gene, 33:137–149; Felenbok B et al, 1988, Gene, 73:385–396; Gwynne et al, 1987, Gene, 51:205–216).

Alcohol dehydrogenase (adh) genes have been investigated in certain plant species. In maize and other cereals they are switched on by anaerobic conditions. The promoter region of adh genes from maize contains a 300 bp regulatory element necessary for expression under anaerobic conditions. However, no equivalent to the alcR regulator protein has been found in any plant. Hence the alcR/alcA type of gene regulator system is not known in plants. Constitutive expression of alcR in plant cells does not result in the activation of endogenous adh activity.

According to a second aspect of the invention, there is provided a chemically-inducible plant gene expression cassette comprising a first promoter operatively linked to an alcR regulator sequence which encodes an alcR regulator protein, and an inducible promoter operatively linked to a target gene which confers herbicide resistance, the inducible promoter being activated by the regulator protein in the presence of an effective exogenous inducer a whereby application of the inducer causes expression of the target gene.

The inducible promoter is preferably derived from the alcA gene promoter but may, alternatively be derived from alcR, aldA or other alcR-induced genes.

We have found that the alcA/alcR switch is particularly suited to drive herbicide tolerance genes for at least the following reasons.

1. The alcA/alcR switch has been developed to drive high levels of gene expression. In addition, the regulatory protein alcR is preferably driven from a strong constitutive promoter such as polyubiquitin. High levels of induced transgene expression, comparable to that from a strong constitutive promoter, such as 35 CaMV, can be achieved.

2. If a gene switch is to be used in a situation where the activating chemical is applied simultaneously with the herbicide, a rapid elevation in the levels of herbicide resistance gene is required. FIG. 1 reveals a time course of marker gene expression (CAT) following application of inducing chemical. This study shows a rapid increase (2 hours) of CAT expression following foliar application of inducing chemical. The immediate early kinetics of induction are brought about be expressing the regulatory protein in constitutive manner, therefore no time lag is encountered while synthesis of transcription factors takes place. In addition we have chosen a simple two component system which does not rely on a complex signal transduction system.

3. We have tested the specificity of alcA/alcR system with a range of solvents used in agronomic practice. A hydroponic seedling system revealed that ethanol, butan-2-ol and cyclohexanone all gave high levels of induced reporter gene expression (FIG. 2). In contrast when the alcohols and ketones listed in Table 1 in which are used in agronomic practice were applied as a foliar spray only ethanol gave high levels of induced reporter gene activity (FIG. 3).

TABLE 1

| | |
|---|---|
| 1. Isobutyl methyl ketone | 13. acetonyl acetone |
| 2. Fenchone | 14. JF5969 (cyclohexanone) |
| 3. 2-heptanone | 15. N-methyl pyrrolidone |
| 4. Di-isobutyl ketone | 16. polyethylene glycol |
| 5. 5-methyl-2-hexanone | 17. propylene glycol |
| 6. 5-methylpentan-2,4-diol | 18. acetophenone |
| 7. ethyl methyl ketone | 19. JF4400 (methylcyclohexanone) |
| 8. 2-pentanone | 20. propan-2-ol |
| 9. glycerol | 21. butan-2-ol |
| 10. γ-butyrolactone | 22. acetone |
| 11. diacetone alcohol | 23. ethanol |
| 12. tetrahydrofurfuryl alcohol | 24. dH$_2$O |

This is of significance since illegitimate induction of transgenes will not be encountered by chance exposure to formulation solvents. Ethanol is not a common component of agrochemical formulations and therefore with appropriate spray management can be considered as a specific inducer of the alc A/R gene switch in a field situation.

4. A range of biotic and abiotic stresses for example pathogen infection, heat, cold, drought, wounding, flooding have all failed to induce the alcA/alcR switch. In addition a range of non-solvent chemical treatments for example salicylic acid, ethylene, absisic acid, auxin, gibberelic acid, various agrochemicals, all failed to induce the alcA/alcR system.

The first promoter may be constitutive or tissue-specific, developmentally-programmed or even inducible. The regulator sequence, the alcR gene, is obtainable from *Aspergilluis nidulans*, and encodes the alcR regulator protein.

The inducible promoter is preferably the alcA gene promoter obtainable from *Aspergilluis nidulans* or a "chimeric" promoter derived from the regulatory sequences of the alcA promoter and the core promoter region from a gene promoter which operates in plant cells (including any plant gene promoter). The alcA promoter or a related "chimeric" promoter is activated by the alcR regulator protein when an alcohol or ketone inducer is applied.

The inducible promoter may also be derived from the aldA gene promoter, the alcB gene promoter or the alcC gene promoter obtainable from *Aspergillus nidulans*.

The inducer may be any effective chemical (such as an alcohol or ketone). Suitable chemicals for use with an alcA/alcR-derived cassette include those listed by Creaser et al (1984, Biochem J, 225, 449–454) such as butan-2-one (ethyl methyl ketone), cylcohexanone, acetone, butan-2-ol, 3-oxobutyric acid, propan-2-ol, ethanol.

The gene expression cassette is responsive to an applied exogenous chemical inducer enabling external activation of expression of the target gene regulated by the cassette. The expression cassette is highly regulated and suitable for general use in plants.

The two parts of the expression cassette may be on the same construct or on separate constructs. The first part comprises the regulator cDNA or gene sequence subcloned into an expression vector with a plant-operative promoter driving its expression. The second part comprises at least part of an inducible promoter which controls expression of a downstream target gene. In the presence of a suitable inducer, the regulator protein produced by the first part of the cassette will activate the expression of the target gene by stimulating the inducible promoter in the second part of the cassette.

In practice the construct or constructs comprising the expression cassette of the invention will be inserted into a plant by transformation. Expression of target genes in the construct, being under control of the chemically switchable promoter of the invention, may then be activated by the application of a chemical inducer to the plant.

Any transformation method suitable for the target plant or plant cells may be employed, including infection by *Agrobacterium tumefaciens* containing recombinant Ti plasmids, electroporation, microinjection of cells and protoplasts, microprojectile transformation and pollen tube transformation. The transformed cells may then in suitable cases be regenerated into whole plants in which the new nuclear material is stably incorporated into the genome. Both transformed monocot and dicot plants may be obtained in this way.

Examples of genetically modified plants which may be produced include field crops, cereals, fruit and vegetables such as: canola, sunflower, tobacco, sugarbeet, cotton, soya, maize, wheat, barley, rice, sorghum, tomatoes, mangoes, peaches, apples, pears, strawberries, bananas, melons, potatoes, carrot, lettuce, cabbage, onion.

The invention further provides a plant cell containing a gene expression cassette according to the invention. The gene expression cassette may be stably incorporated in the plant's genome by transformation. The invention also provides a plant tissue or a plant comprising such cells, and plants or seeds derived therefrom.

The invention further provides a method for controlling plant gene expression comprising transforming a plant cell with a chemically-inducible plant gene expression cassette which has a first promoter operatively linked to an alcR regulator sequence which encodes an alcA regulator protein, and an inducible promoter operatively linked to a target gene which confers herbicide resistance, the inducible promoter being activated by the regulator protein in the presence of an effective exogenous inducer whereby application of the inducer causes expression of the target gene.

This strategy of inducible expression of herbicide resistance can be achieved with a pre-spray of chemical activator or in the case of slow acting herbicides, for example N-phosphonomethyl-glycine (commonly known as glyphosate), the chemical inducer can be added as a tank mix simultaneously with the herbicide.

This strategy can be adopted for any resistance conferring gene/corresponding herbicide combination. For example, the alcA/alcR gene switch can be used with:

1. Maize glutathione S-transferase (GST-27) gene (see our International Patent Publication No WO90/08826), which confers resistance to chloroacetanilide herbicides such as acetochlor, metolachlor and alachlor.
2. Phosphinotricin acetyl transferase (PAT), which confers resistance to the herbicide commonly known as glufosinate.
3. Acetolactate synthase gene mutants from maize (see our international Patent Publication No WO90/14000) and other genes, which confer resistance to sulphonyl urea and imadazlonones.
4. Genes which confer resistance to glyphosate. Such genes include the glyphosate oxidoreductase gene (GOX) (see International Patent Publication No. WO92/00377 in the name of Monsanto Company); genes which encode for 5-enolpyruvyl-3-phosphoshikimic acid synthase (EPSPS), including Class I and Class II EPSPS, genes which encode for mutant EPSPS, and genes which encode for EPSPS fusion peptides such as that comprised of a chloroplast transit peptide and EPSPS (see for example EP 218 571, EP 293 358, WO91/04323, WO92/04449 and WO92/06201 in the name of Monsanto Company); and genes which are involved in the expression of CPLyase.

Various further preferred features and embodiments of the present invention will now be described in the non-limiting examples set out below and with reference to the drawings in which:

FIG. 6 is a summary of the cassettes and specific plant transformation constructs;

FIG. 7 illustrates the chloroplast transit sequence 1 from Arabidopsis RUBISCO (CPT 1)(SEQ ID NO: 1–SEQ ID NO: 6);

FIG. 8 shows the sequence of plasmid pMJB1 (SEQ ID NO: 8 and SEQ ID NO: 9);

| | |
|---|---|
| ADH$_i$ | Alcohol dehydrogenase from maize; |
| PAT | Phosphinothricin acetyl transferase (Basta resistance gene); |
| AMP | Ampicillin resistance gene; |
| CaMV 35S | Cauliflower mosaic virus 35S promoter; |
| nos Poly A | Nopalaine synthase poly A region; |
| ori | ColE1 origin of replication from pUC |

Figure 13:
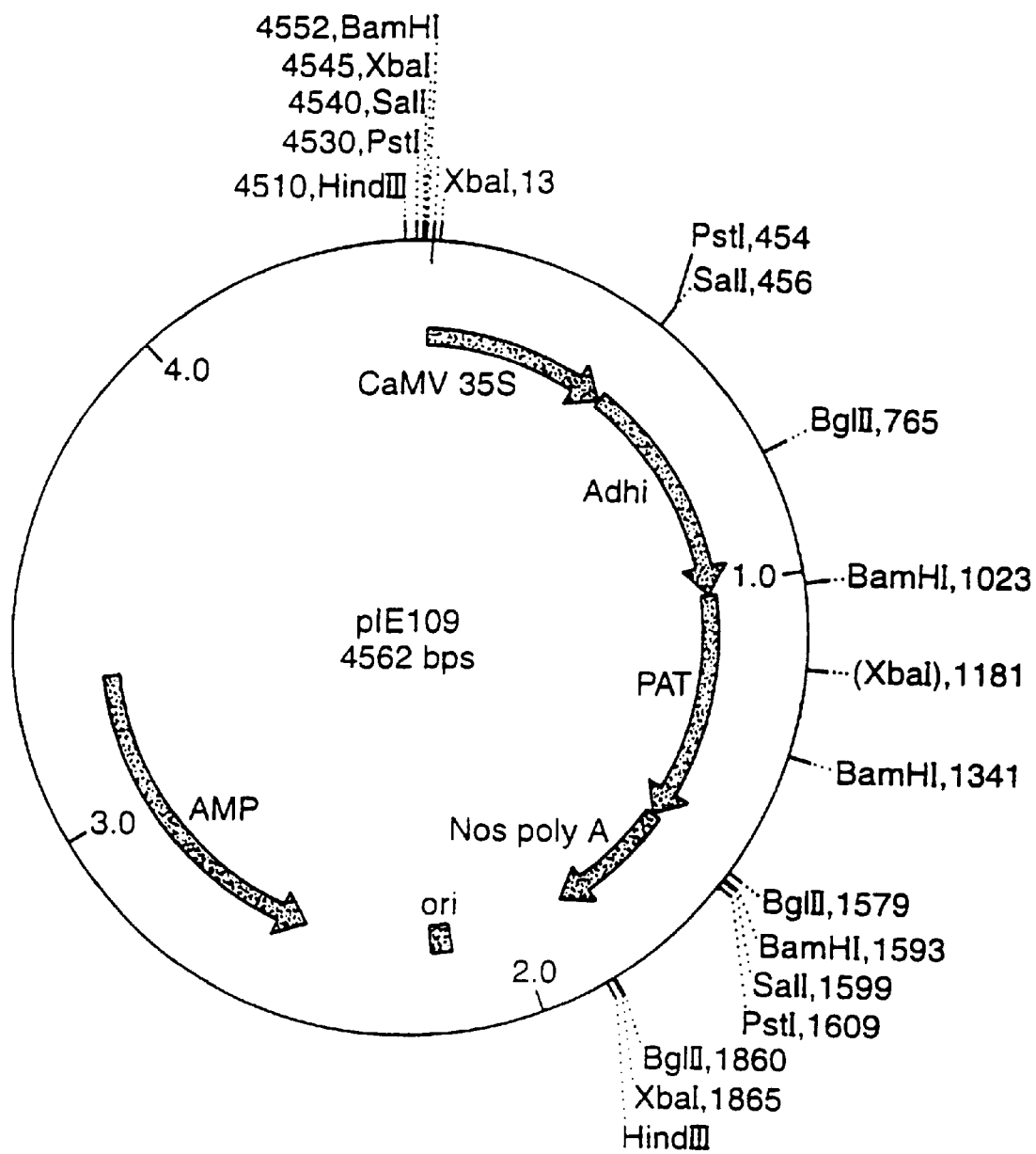
FIG. 13 is a map of plasmid pIE109 in which the numbers are in base pairs (not to scale) and the following abbreviations are used.
Figure 14:
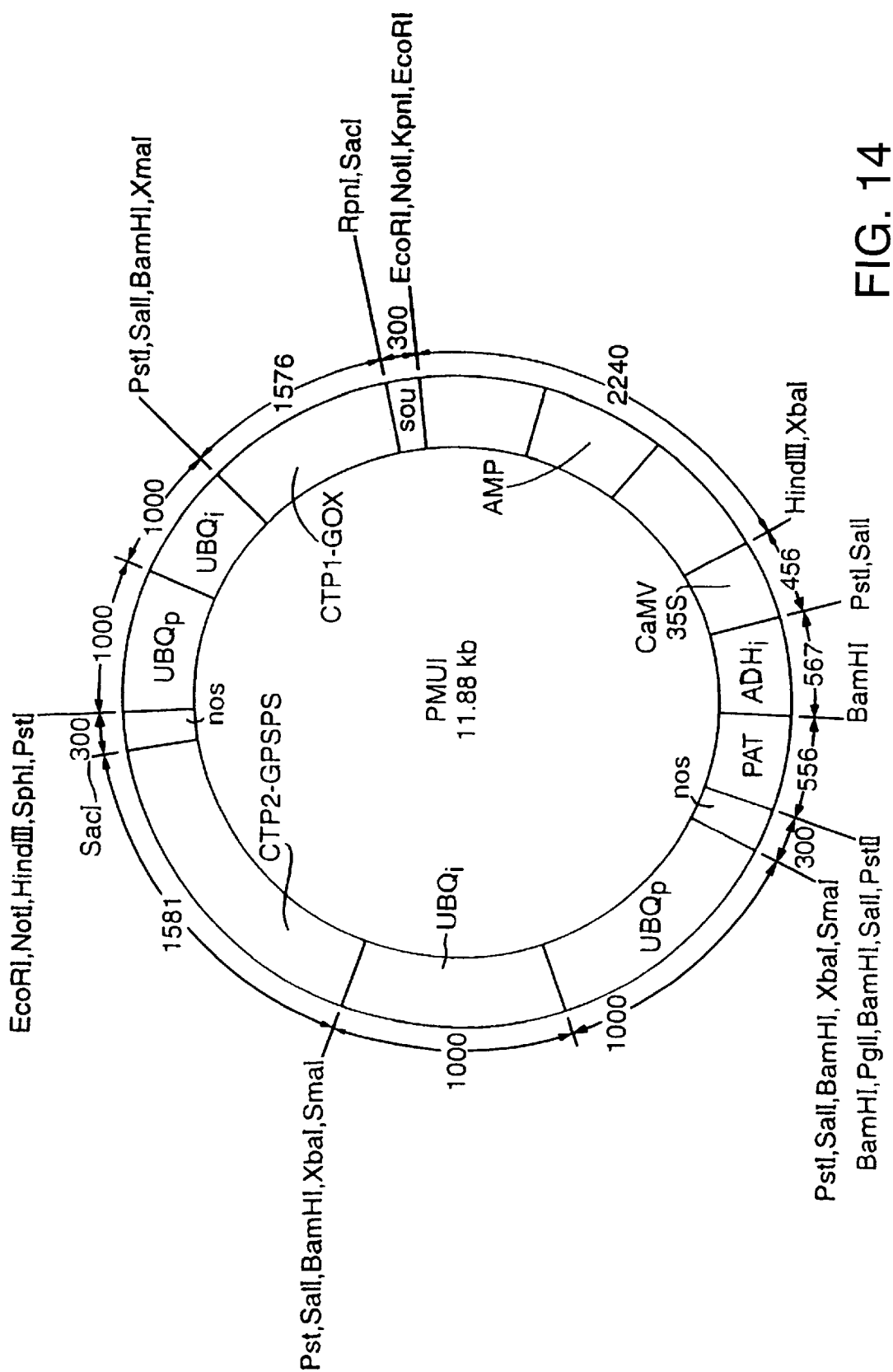

FIG. 14 is a map of plasmid pMV1 in which the numbers are in base pairs (not drawn to scale) and the abbreviations are as for FIG. 13 with the following additional abbreviations:

| | |
|---|---|
| UBQ$_p$ | Maize ubiquitin promoter; |
| UBQ$_i$ | Maize ubiquitin intron; |
| nos | Nopaline synthase 3' terminator; |
| CZP1 GOX | Chloroplast transit peptide - glyphosate oxidase sequence; |
| CZP2 GPSPS | Chloroplast transit peptide - EPSP synthetase sequence; |

Figure 15:
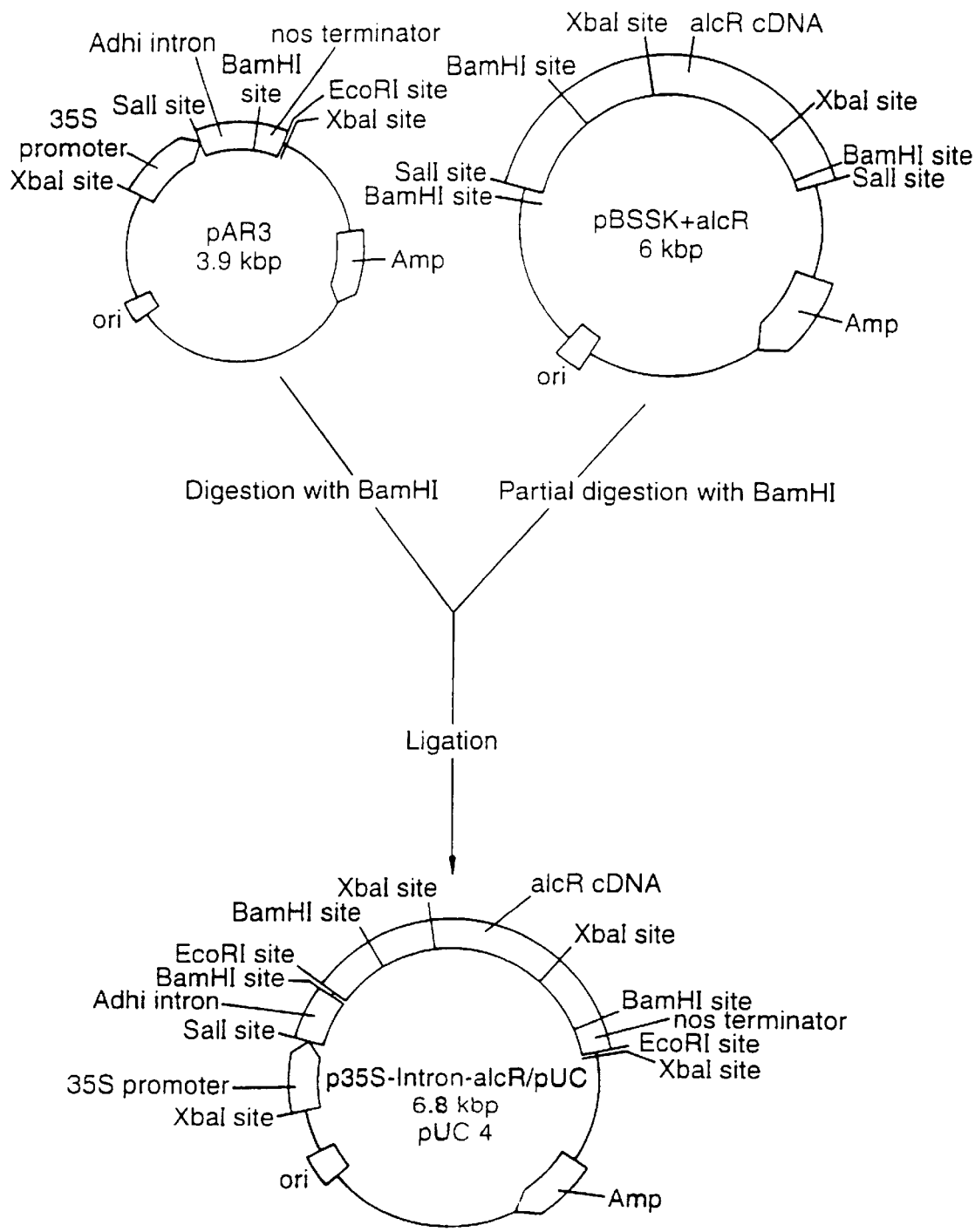
Figure 16:
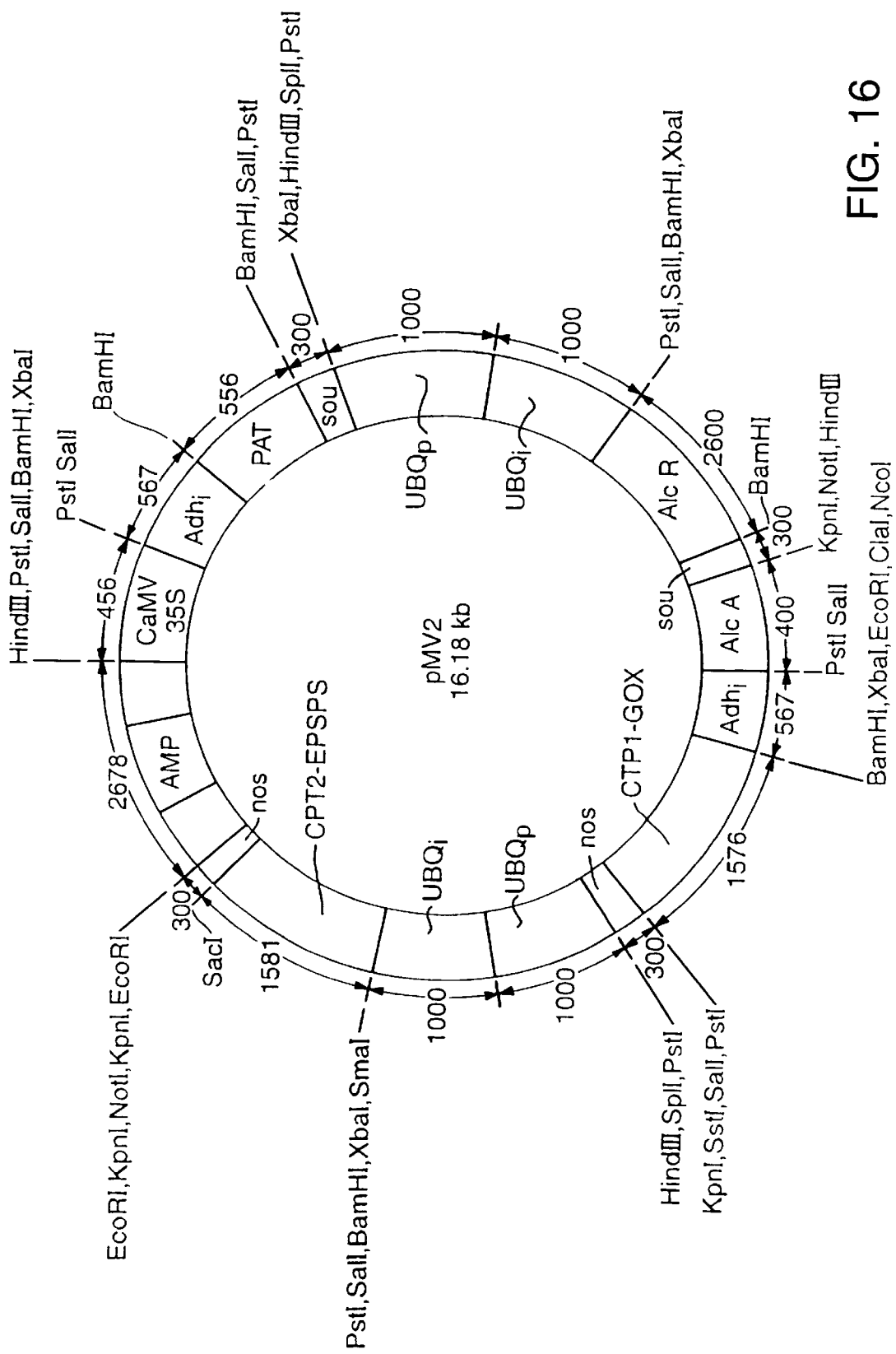

FIG. 15 shows the preparation of plasmid pUC4 by ligation of pAr3 and pBSSK;

FIG. 16 is a map of plasmid pMV2 in which the numbers are in base pairs (not drawn to scale) and the abbreviations are as for FIG. 14 with the following additional abbreviations:

| | |
|---|---|
| AlcA | *Aspergillus nidulans* alcA promoter; |
| AlcR | *Aspergillus nidulans* alcR promoter; |

Figure 17:
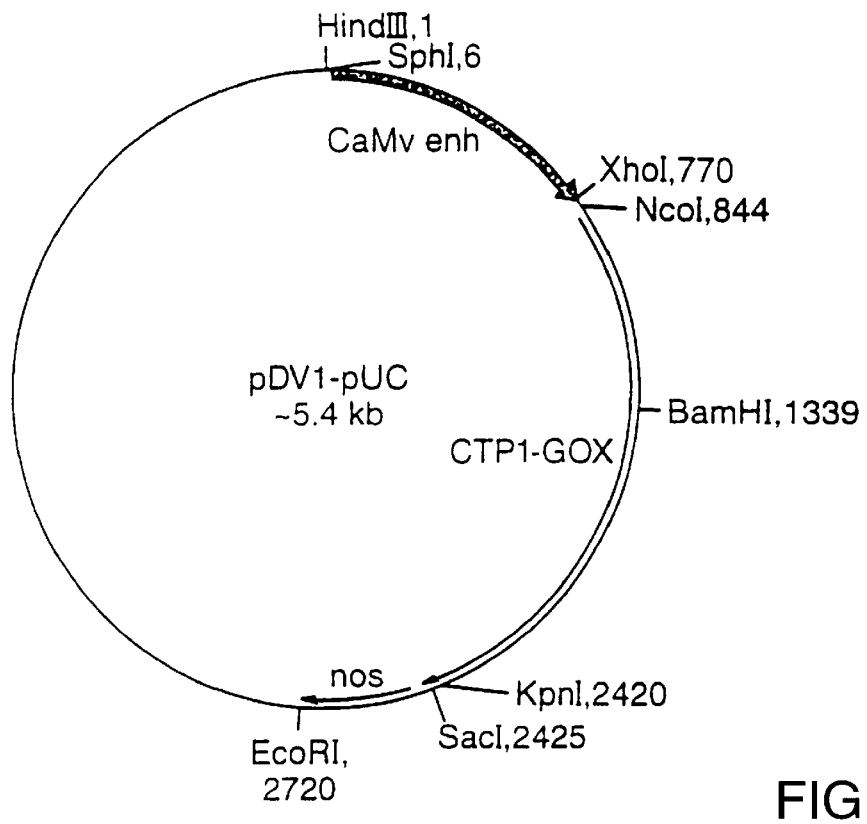
Figure 18:
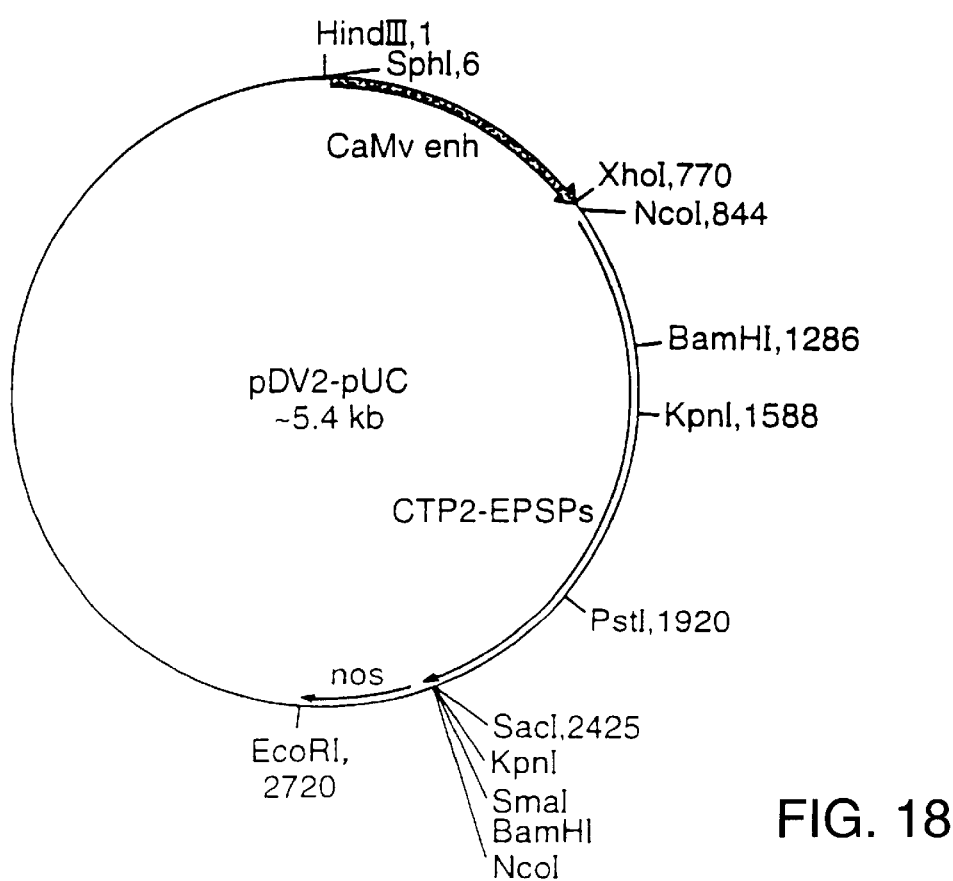
Figure 19:
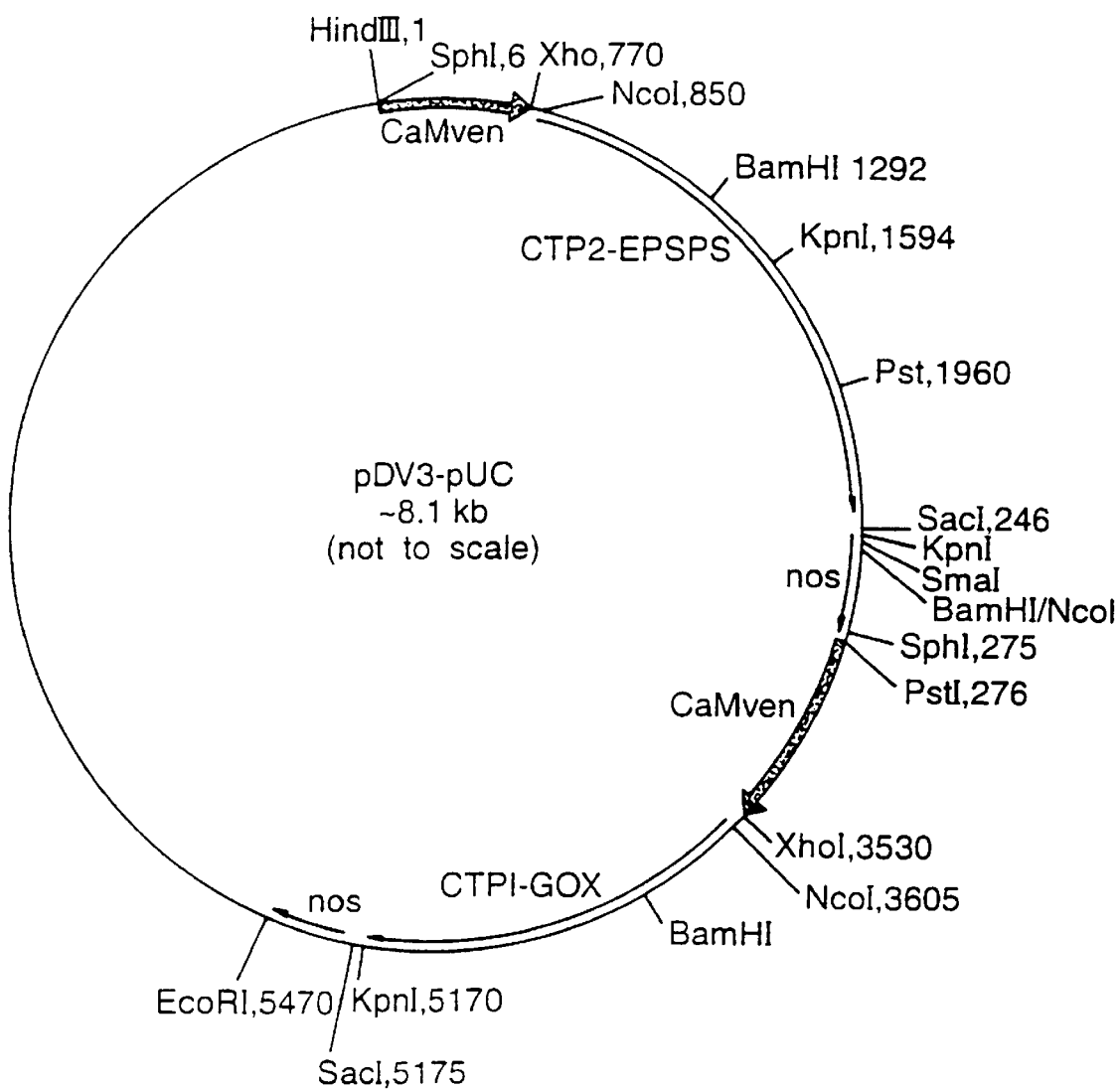
Figure 20:
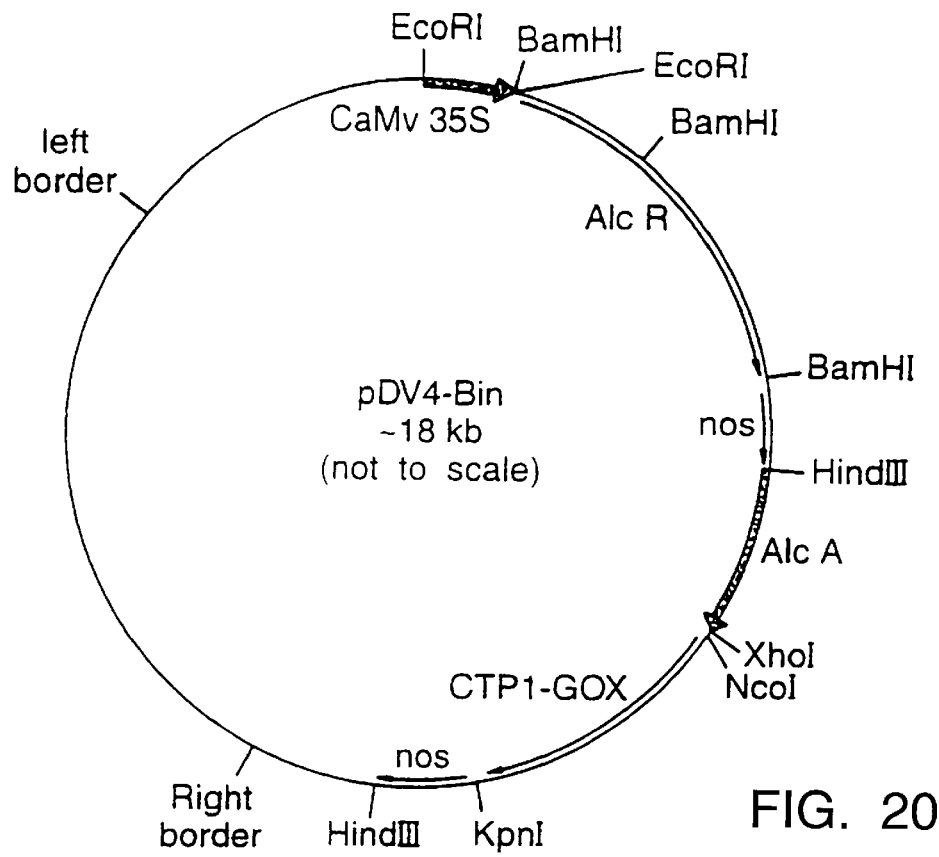
Figure 21:
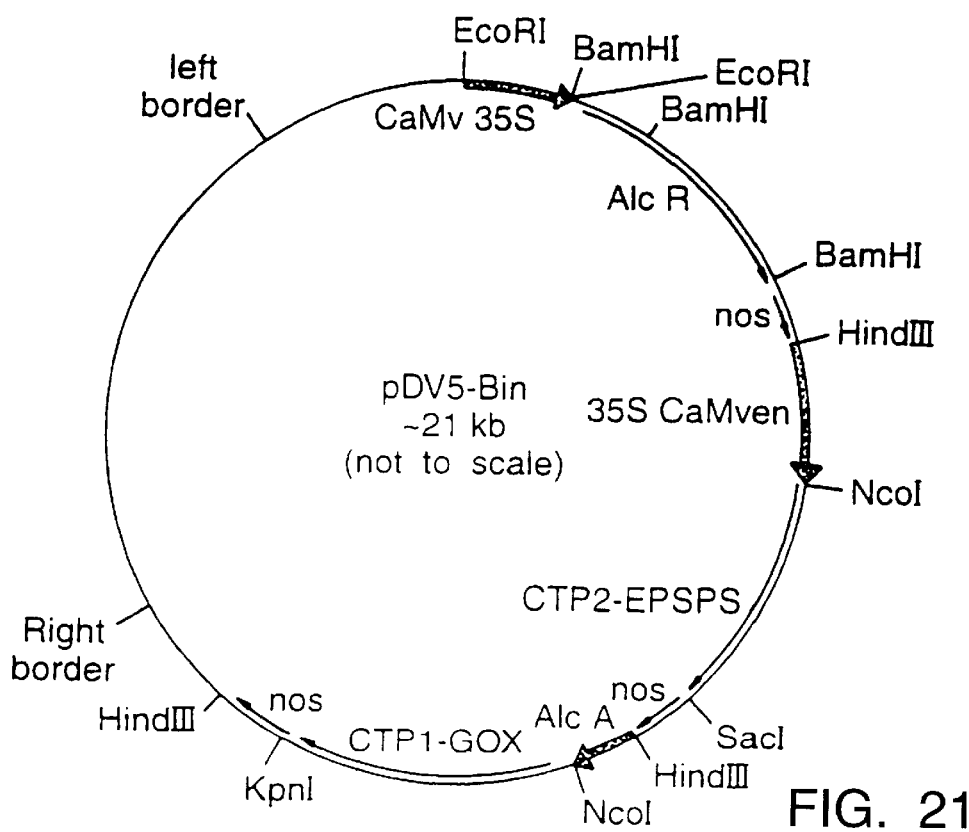

FIG. 17 is a map of plasmid pDV1-pUC;

FIG. 18 is a map of plasmid pDV2-pUC;

FIG. 19 is a map of plasmid pDV3-pUC;

FIG. 20 is a map of plasmid pDV4-Bin;

FIG. 21 is a map of plasmid pDV5-Bin; and

Figure 22:
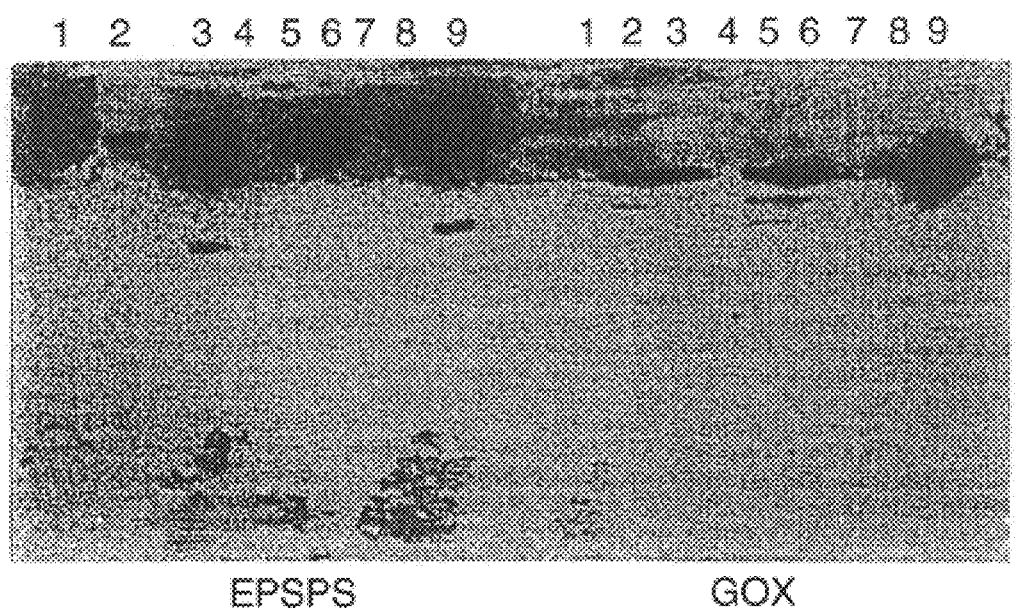

FIG. 22 is a western Blot showing the expression of EPSPS and GOX in transformants.

EXAMPLES

We have chosen to exemplify the alcA/alcR gene switch with genes conferring resistance to glyphosate. The switch will be used to drive inducible expression of glyphosate oxidase (GOX) in plants. Switchable GOX has been expressed alone or in conjunction with constitutive expression of 5-enol-pyruvylshikimate 3-phosphate (EPSPS) CP4. Constructs have been optimised for expression in monocotyledonous and dicotyledonous crop species.

Example 1

Production Of The alcR Regulator Construct

The alcR genomic DNA sequence has been published, enabling isolation of a sample of alcR cDNA.

The alcR cDNA was cloned into the expression vectors pJR1(pUC). pJR1 contains the Cauliflower Mosaic Virus 35S promoter. This promoter is a constitutive plant promoter and will continually express the regulator protein. The nos polyadenylation signal is in the expression vector.

Figure 1:
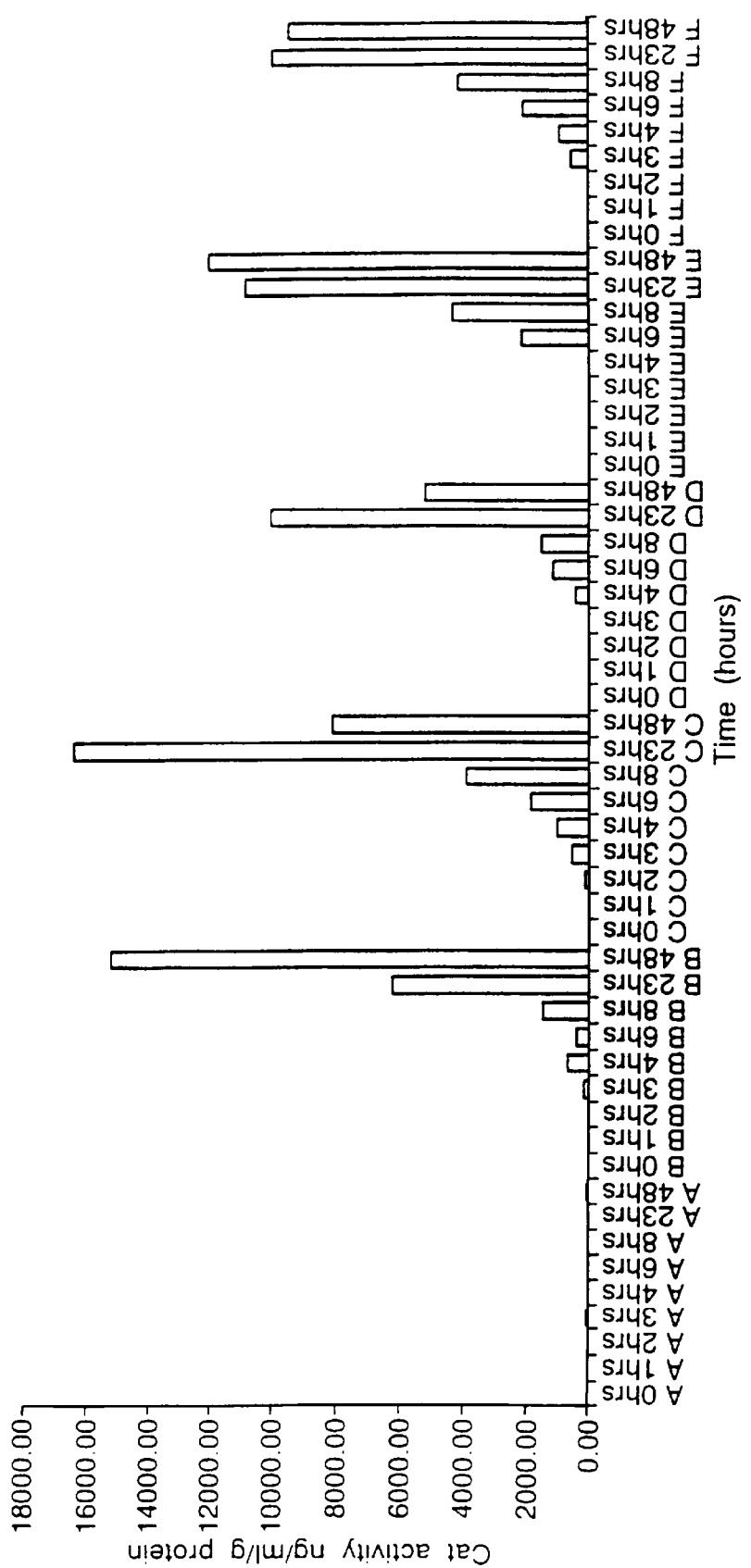
FIG. 1 illustrates the time course of marker gene expression (CAT) following application of inducing chemical.
Figure 2:
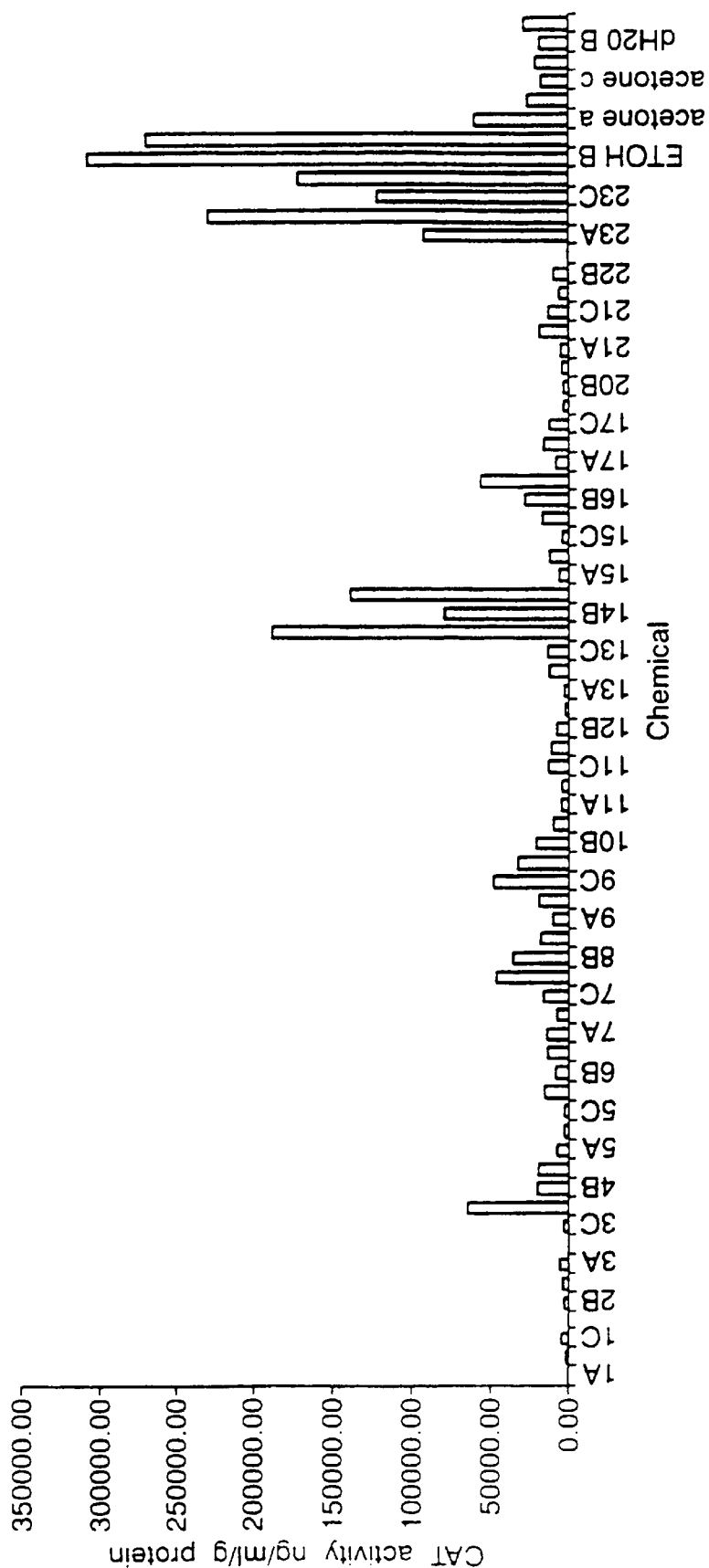
FIG. 2 illustrates the levels of induced reporter gene expression on root drenching with a range of solvents.
Figure 3:
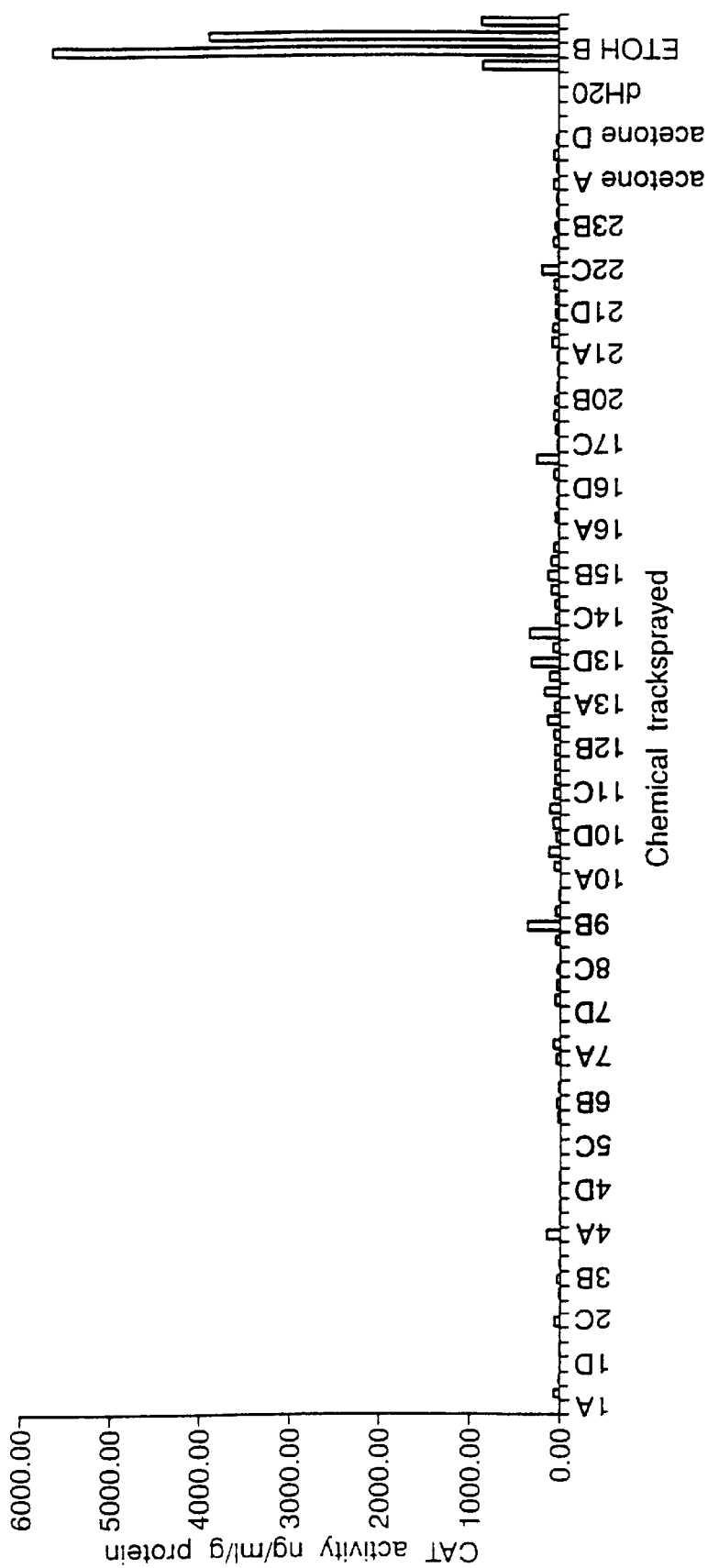
FIG. 3 illustrates the levels of induced reporter gene activity when the chemicals listed in Table 1 were applied as a foliar spray.
Figure 4A:
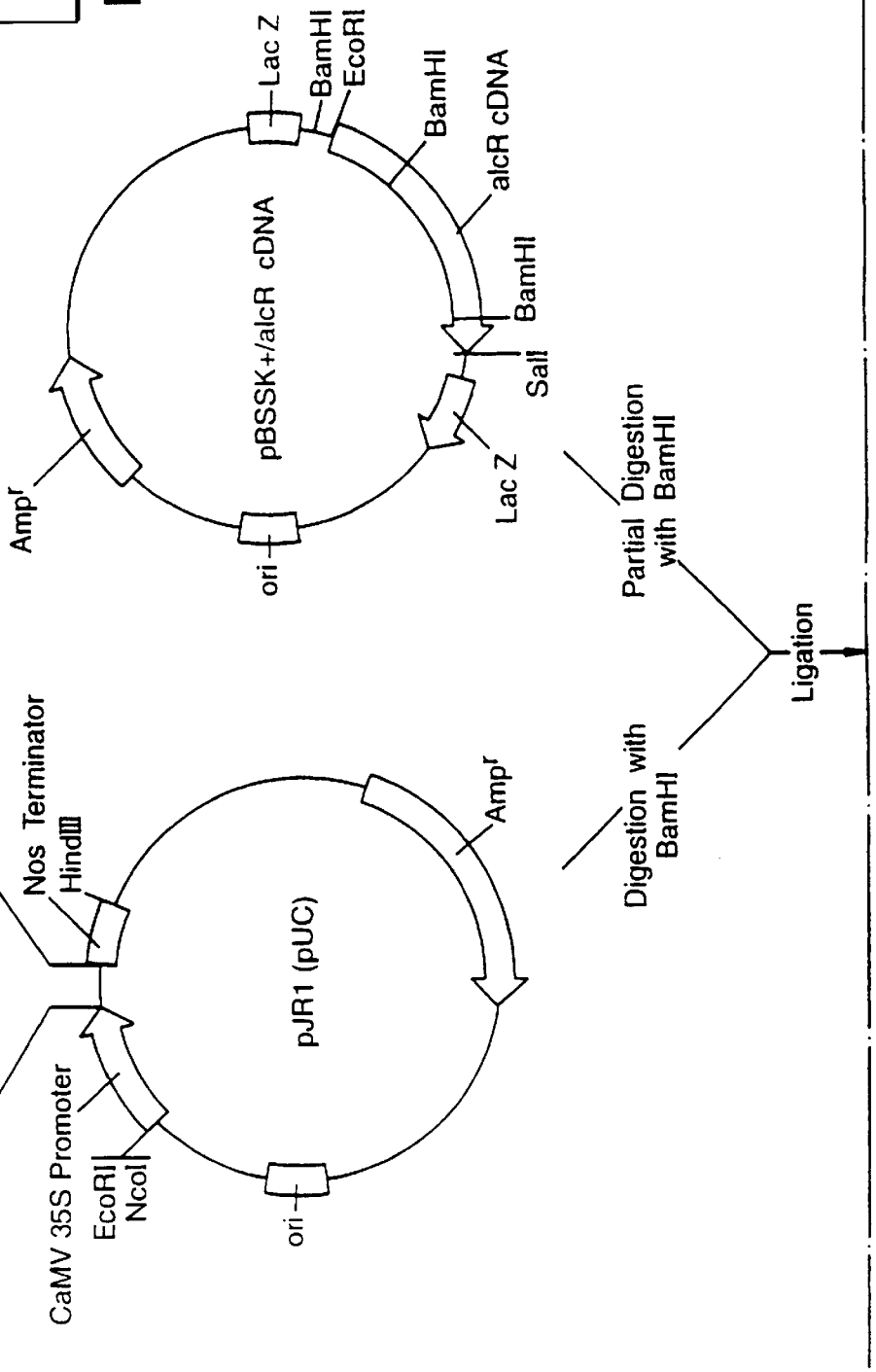
FIG. 4 illustrates the production of the 35S regulator construct by ligation of alcR cDNA into pJRI.
Figure 4B:
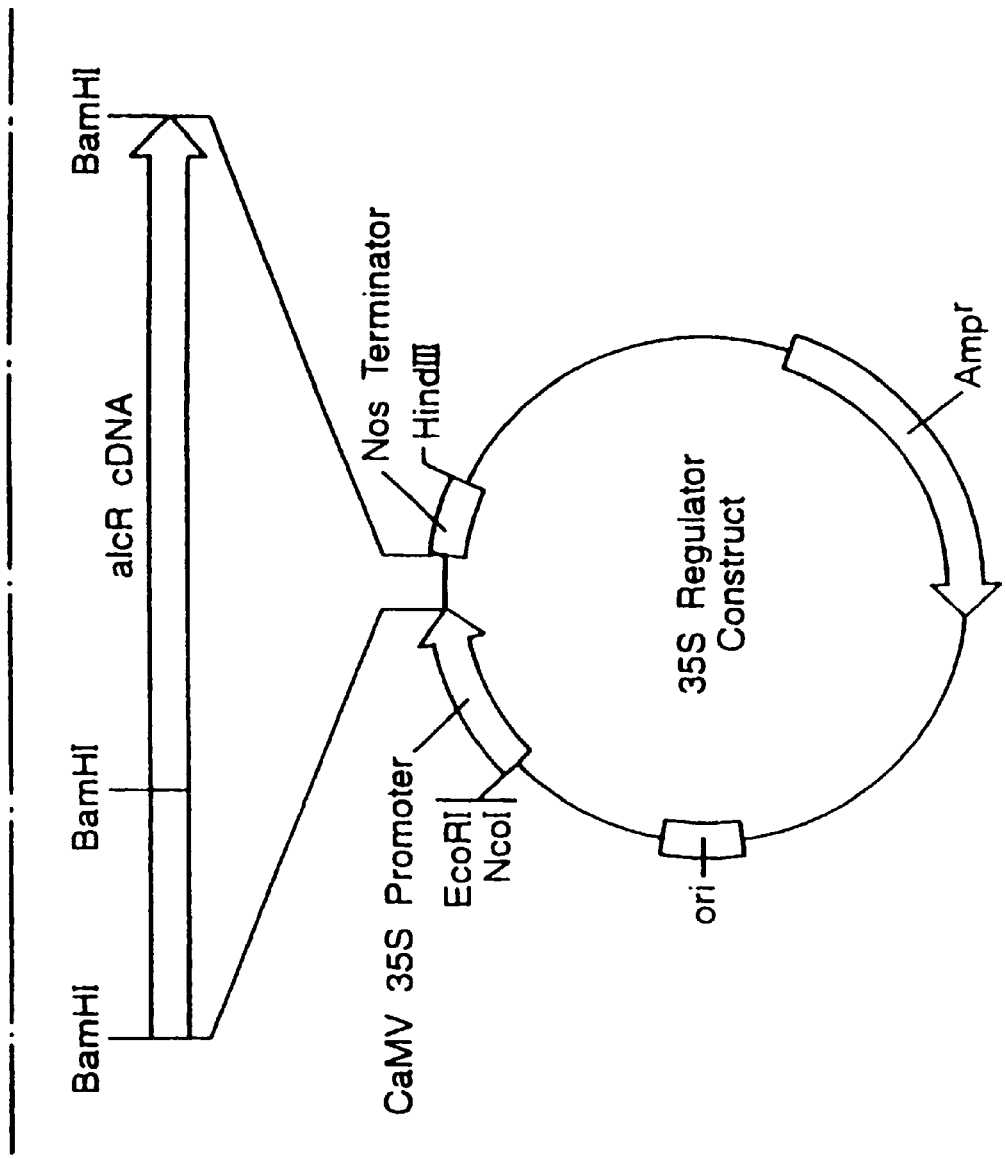

FIG. 4 illustrates the production of the 35S regulator construct by ligation of alcR cDNA into pJR1. Partial restriction of the alcR cDNA clone with BamHI was followed by electrophoresis in an agarose gel and the excision and purification of a 2.6 Kb fragment. The fragment was then ligated into the pJR1 vector which had been restricted with BamHI and phosphatased to prevent recircularisation. The alcR gene was thus placed under control of the CaMV 35S promoter and the nos 3' polyadenylation signal in this "35S-alcR" construct.

Example 2

Production Of The alcA-CAT Reporter Construct Containing The Chimeric Promoter

The plasmid pCaMVCN contains the bacterial chloramphenicol transferase (CAT) reporter gene between the 35S promoter and the nos transcription terminator (the "35S-CAT" construct).

The alcA promoter was subcloned into the vector pCaMVCN to produce an "alcA-CAT" construct. Fusion of part of the alcA promoter and part of the 35S promoter created a chimeric promoter which allows expression of genes under its control.

Figure 5A:
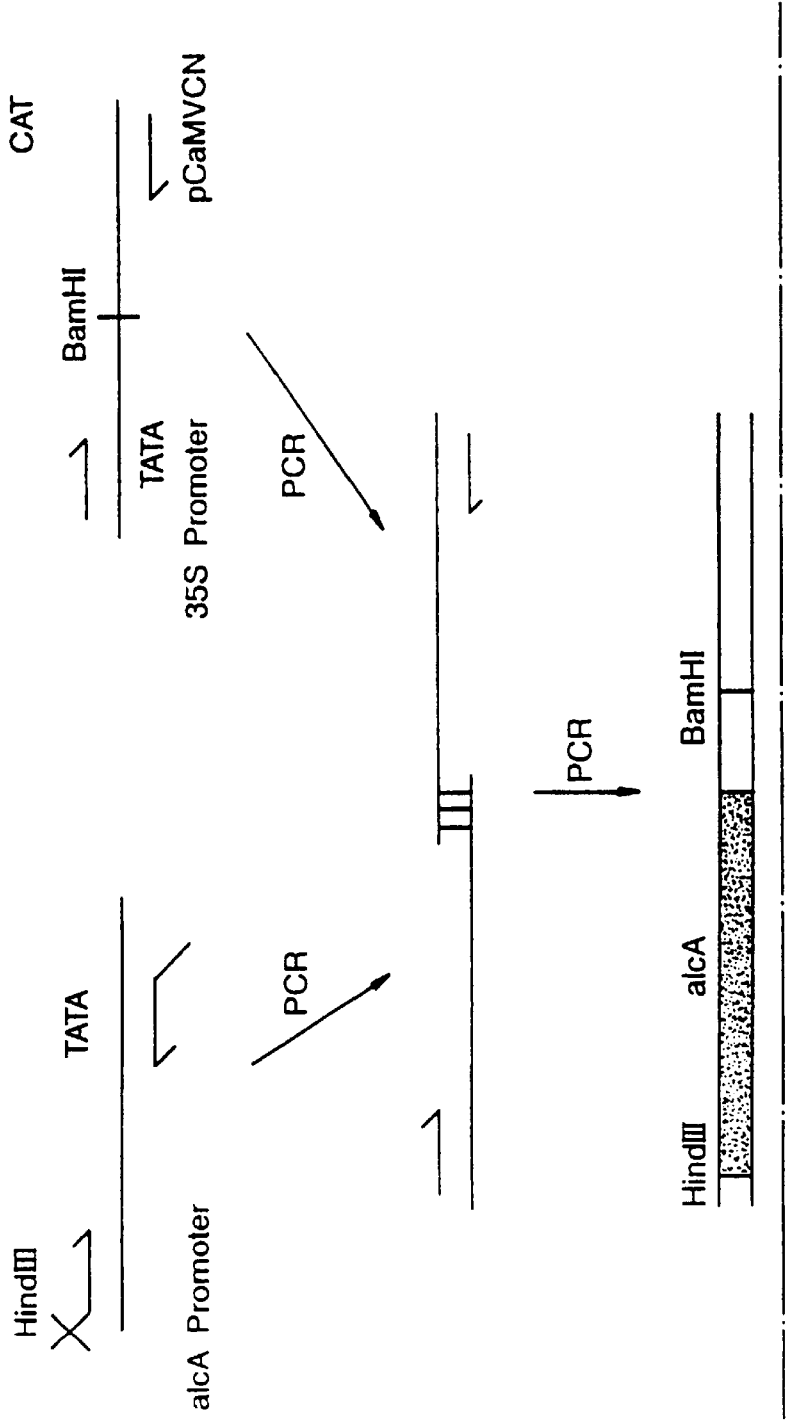
FIG. 5 illustrates the production of the reporter construct.
Figure 5B:
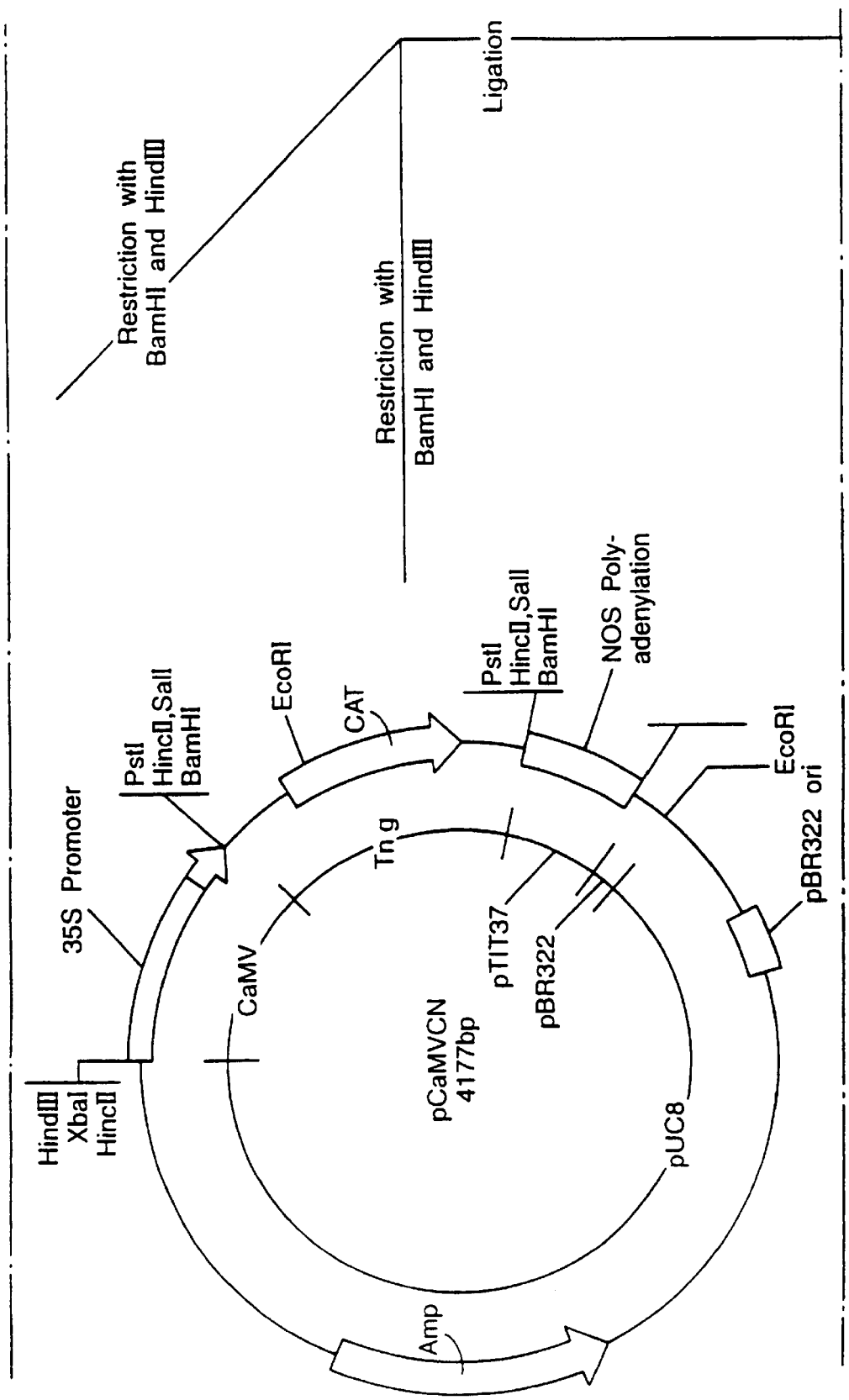
Figure 5C:
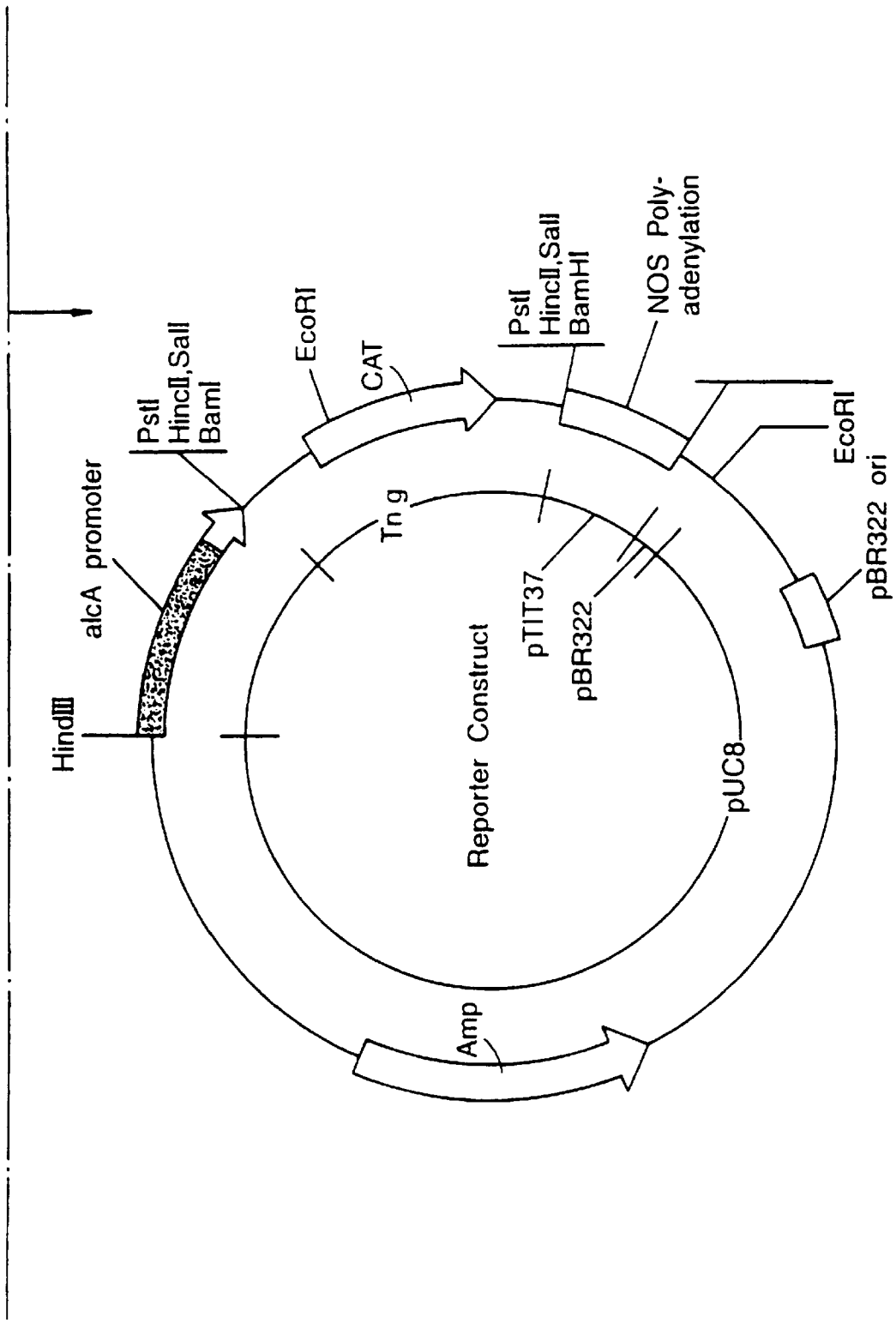

FIG. 5 illustrates the production of the reporter construct. The alcA promoter and the 35S promoter have identical TATA boxes which were used to link the two promoters together using a recombinant PCR technique: a 246 bp region from the alcA promoter and the 5' end of the CAT gene from pCaMVCN (containing part of the −70 core region of the 35S promoter) were separately amplified and then spliced together using PCR. The recombinant fragment was then restriction digested with BamHI and HindIII. The pCaMVCN vector was partially digested with BamHI and HindIII, then electrophoresed so that the correct fragment could be isolated and ligated to the recombinant fragment.

The ligation mixtures were transformed into *E coli* and plated onto rich agar media. Plasmid DNA was isolated by miniprep from the resultant colonies and recombinant clones were recovered by size electrophoresis and restriction mapping. The ligation junctions were sequenced to check that the correct recombinants had been recovered.

Example 3

Glypliosate Resistance Constructs

A summary of the cassettes and specific plant transformation constructs is shown in FIG. 6.

Dicot Vector 1

Vector 1 is a constitutive control plasmid containing the glyphosate oxidase gene (GOX) fused to the chloroplast transit sequence 1 from Arabidopsis RUBISCO (CPT 1) (FIG. 7) driven by the enhanced 35S CaMV promoter (ES) and the TMV omega translational enhancer sequence (TMV). Vector 1 utilizes the nopoline synthase terminator (nos). The synthetic GOX gene with the addition of CTP 1 was synthesised with information from patent publication WO92/00377 with addition of NcoI site at the translation start ATG, and a Kpn I at the 5' end. Internal Sph I sites and NcoI site were deleted during synthesis with no change in amino acid usage. The CTP 1 GOX synthesised sequence was isolated as a Nco I Kpn I fragment and ligated using standard molecular cloning techniques into NcoI KpnI cut pMJB1, a plasmid based on pIBT 211 containing the CaMV 35 promoter with duplicated enhancer linked to the tobacco mosaic virus translational enhancer sequence replacing the tobacco etch virus 5' non-translated leader, and terminated with the nopaline synthase poly (A) signal (nos) (FIG. 8).

Figure 9:
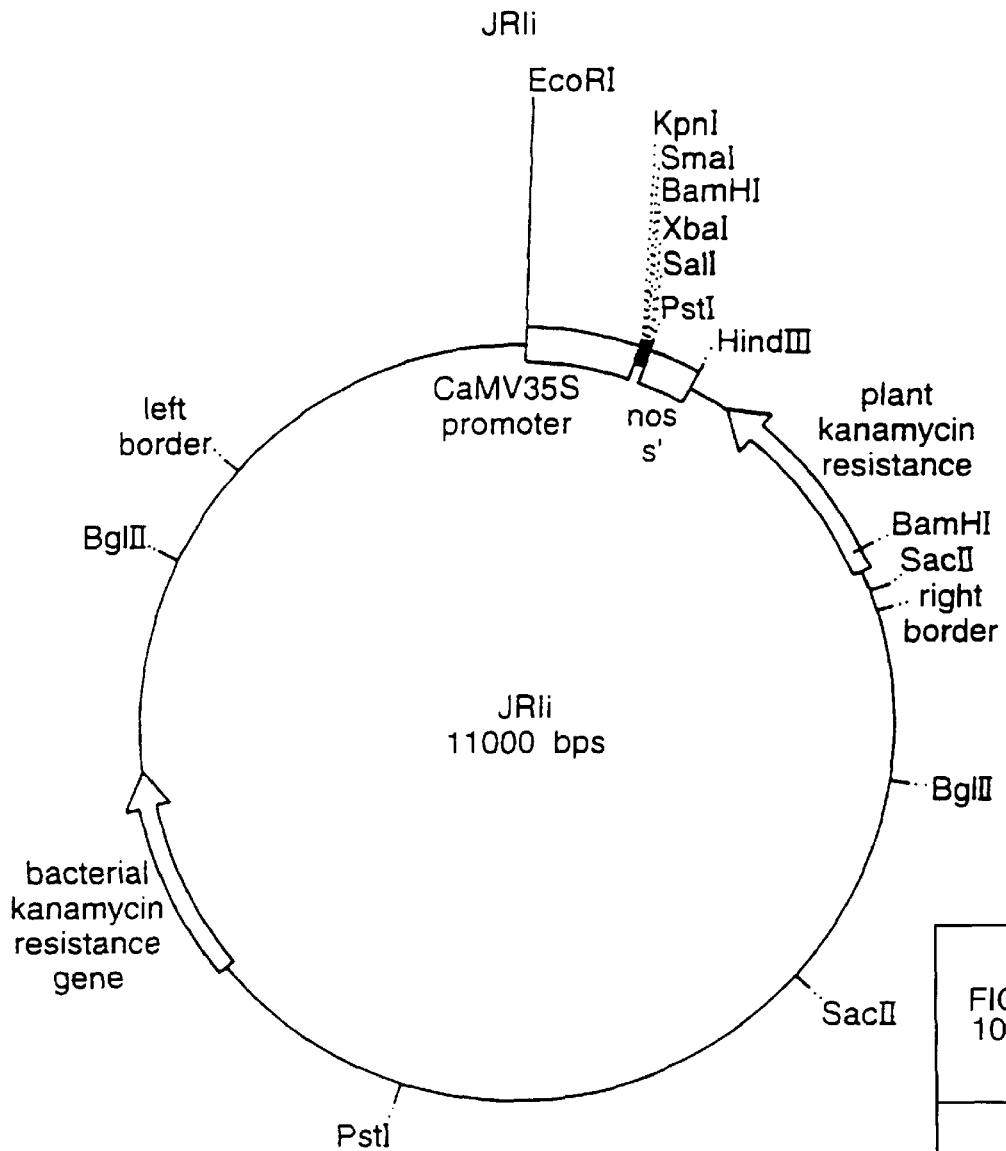
FIG. 9 is a map of plasmid pJRIi.

A cassette containing enhanced 35 CaMV TMV sequence CTP 1 GOX and nos terminator (dicot vector 1 pUC FIG. 17) was isolated as a HindIII EcoRII fragment and ligated into Hind III EcoRI cut pJRIi, a Bin 19 base plant transformation vector (FIG. 9).

Dicot Vector 2

Figure 10:
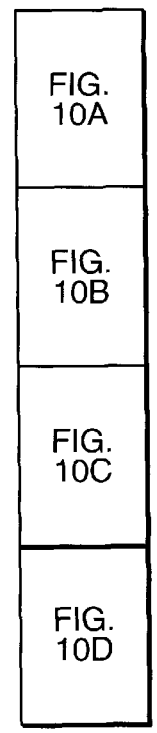
FIG. 10 illustrates the chloroplast transit sequence CTP2 from EPSPS class I gene from *Petunia hybrida* (SEQ ID NO: 10–SEQ ID NO:15)
Figure 11:
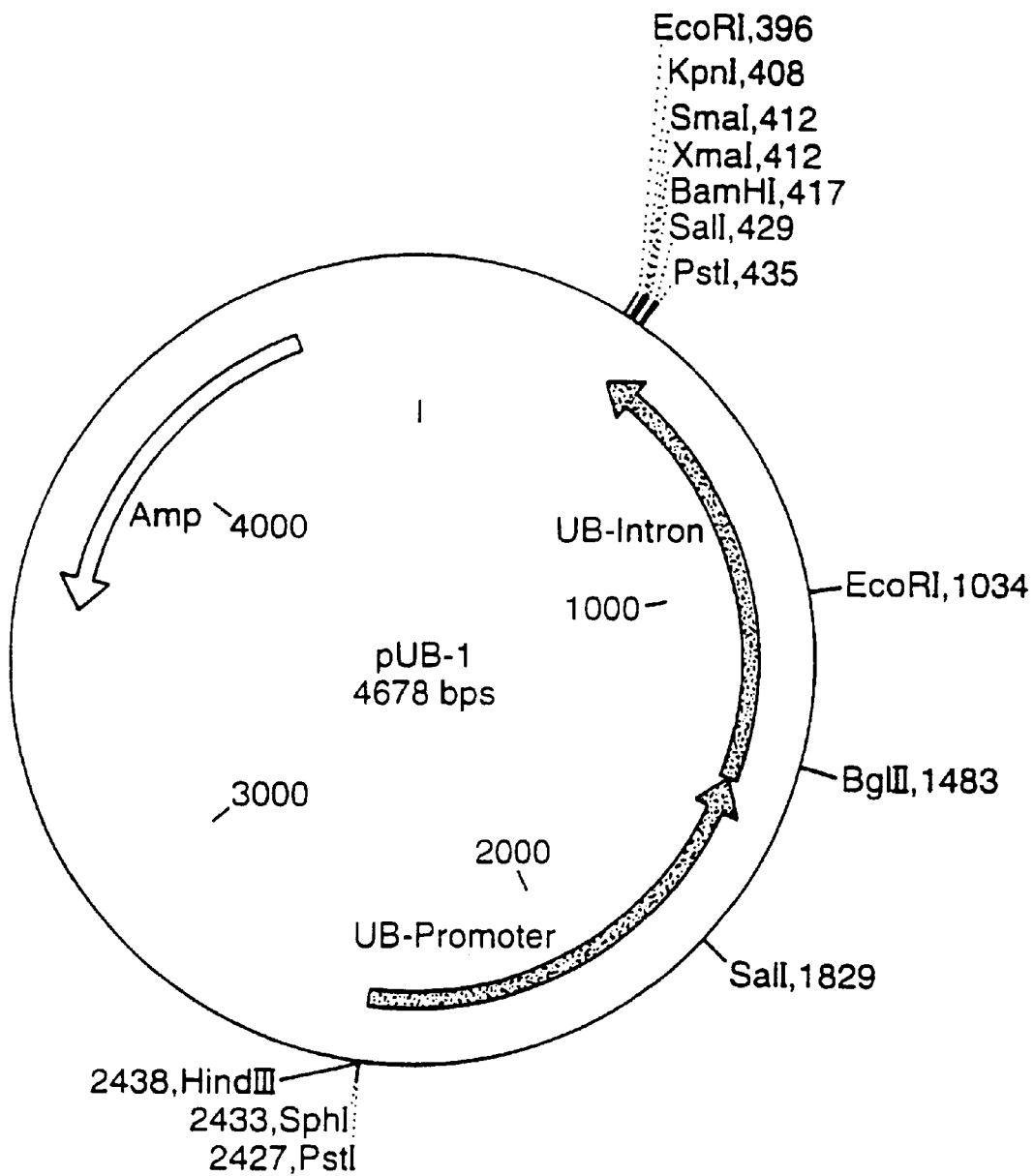
FIG. 11 is a map of plasmid pUB-1.

The synthetic EPSPS CP4 gene, fused to the chloroplast transit sequence CTP2 (FIG. 10) from EPSPS class I gene from Petunia hybrida, was synthesised with data from patent WO 92/04449 with NcoI at the translation initiation ATG. A internal Sph I site was silenced in the EPSPS CP4 gene with no change of amino acid usage.

A fragment containing the synthetic CTP 2 CP4 EPSPS was isolated as a NcoI Sac I fragment and ligated in to pMJBI. A fragment containing the CaMV 35 promoter with a duplicated enhancer, TMV omega sequence CTP 2 transit peptide, EPSPS and nos terminator was isolated as a EcoRI Hind III fragment (dicot vector 2 pUC FIG. 18)and cloned into pJRIi to give dicot vector 2 pUC (FIG. 18).

Upon sequencing the junctions of dicot vector 2, an additional sequence was identified inserted between the SacI site and the beginning of the nos terminator. This was as follows:

5' AGG CTG CTT GAT GAG CTC GGT ACC CGG GGA TCC ATG GAG CCG AAT 3' (SEQ ID NO: 16)

Dicot Vector 3

A control vector with both EPSPS and GOX genes was constructed by cutting dicot vector 2 with EcoRI and inserting an ΔEcoRI Sph I ΔEcoRI linker. The sequence of the linker is shown below:

5' AAT TAG GGG CAT GCC CCT 3' (SEQ ID NO: 17)

The resultant vector was cut with Sph I to liberate the cassette B which was cloned into an SphI site in dicot vector 1), 5' to the 35 CaMV promoter. Cassettes 1) and 2) were then excised as a HindIII and EcoRI fragment from dicot vector 3-pUC (FIG. 19) and cloned in to pJRIi.

Dicot Vector 4

An inducible GOX vector was constructed by excising the CAT gene from "palcCAT" as PstI fragment. The vector band, containing the alcA promoter and nos terminator was gel purified and used in ligations with a PstI-XhoI-KpnI-PstI linker, the sequence of which is as follows:

5' GCC ACT CGA GCT AGG TAC CCT GCA 3' (SEQ ID NO: 18)

The orientation of this was confirmed by sequence analysis. The TMV omega and CTPI GOX sequence from dicot vector 1) were isolated as a XhoI KpnI fragment and cloned into the alcA nos vector containing the XhoI-KpnI-PstI linker. The alcA TMV CTP1 GOX nos cassette was excised as a HindIII fragment and cloned into the plant transformation vector "p35S-alc R", containing the alcR cDNA nos terminator under the control of the 35 CaMV promoter to form dicot vector 4 (FIG. 20).

Dicot Vector 5

Dicot vector 5 (FIG. 22) containing inducible GOX and constitutive EPSPS genes was prepared using the following cloning strategy. Dicot vector 2 (pDV2-pUC) was modified by cloning in a ΔEcoRI-HindIII-ΔEcoRI linker into the EcoRI site to allow excision of the CaMV en-CTP2-EPSPS-nos cassette as a HindIII fragment. This fragment was then ligated into HindIII cut pDV4-Bin. Recombinants containing all three cassettes ie 35S-AlcR, CaMVen-CTP2-EPSPS-nos and AMcA-CTP1-GOX-nos were selected by hybridization with radiolabelled oligonucleotides. Confirmation of orientation was done by sequencing across all borders.

Monocot Vectors

Vector 1: Cassette D

Figure 12:
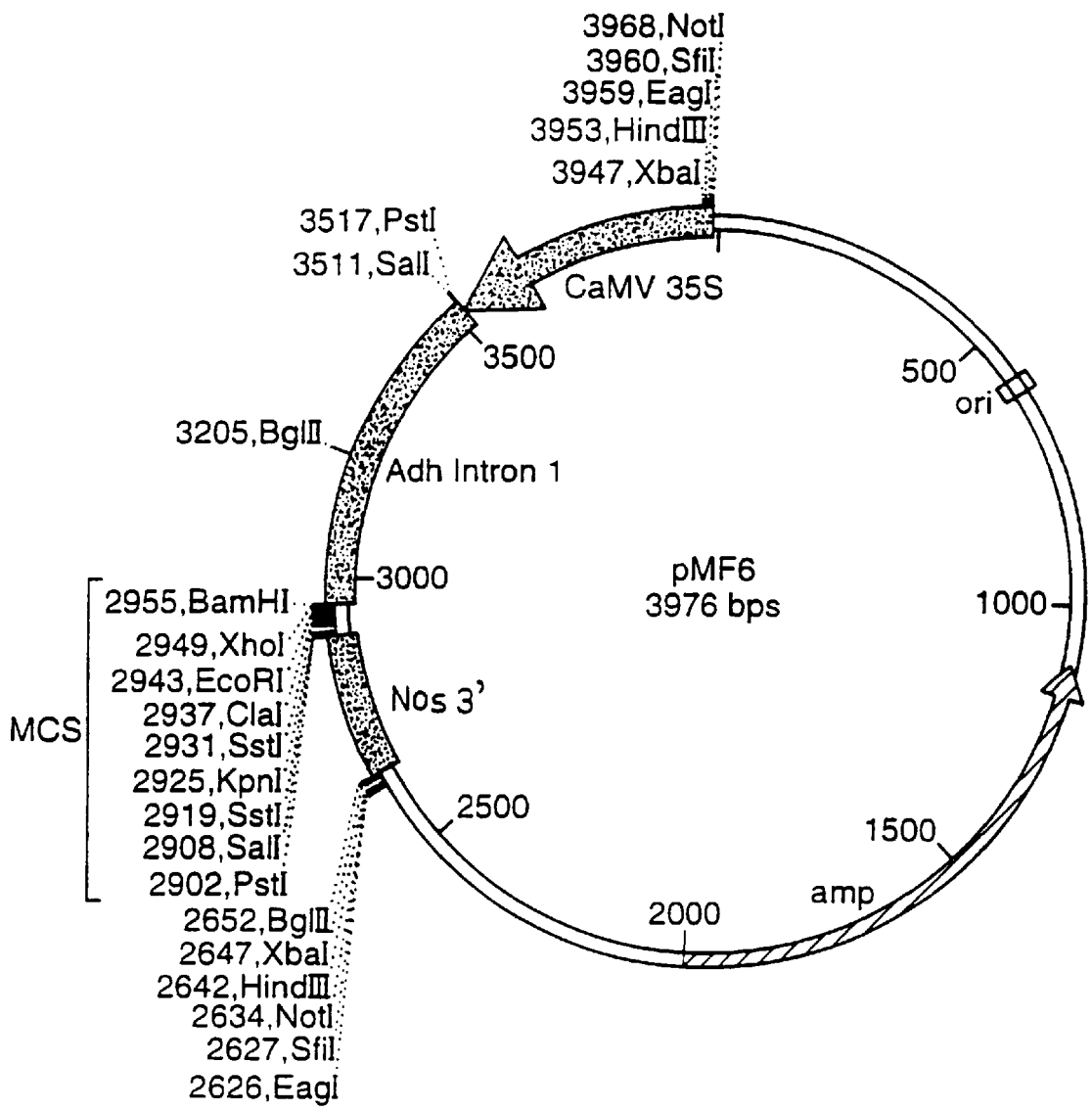
FIG. 12 is a map of plasmid pMF6.

An EcoRI-NotI-EcoRI linker (5'AATTCATTTGCGGCCGCAAATG3')(SEQ ID NO: 19) was inserted into dicot vector pDVI. The plasmid was cut with NcoI and the 5' overhang filled-in with DNA Polymerase I Klenow fragment. The linear vector was then cut with NotI and the resulting blunt/NotI fragment containing the CTP1 GOX and nos terminator was ligated into a SmaI/NotI digested pPUB1 vector (FIG. 12) containing the polyubiquitin promoter, polyubiquitin intron with a KpnI-NotI-KpnI linker (5'CATTTGCGGCCGCAAATGGTAC3') (SEQ ID NO: 20) insertion. A HindIII-NotI-HindIII linker (5'AGCTTGCAGCGGCCGCTGCA3')(SEQ ID NO: 21) was inserted into the resulting construct.

Vector 1: Cassette E

An EcoRI-NotI-EcoRI linker (5'AATTCATTTGCGGCCGCAAATG3')(SEQ ID NO:19) was inserted into dicot vector pDV2. The plasmid was cut with NcoI and the 5' overhang filled-in with DNA Polymerase I Kienow fragment. The linear vector was then cut with NoII and the resulting blunt/NotI fragment containing the CTP2 EPSPS and nos terminator was ligated into a SmaI/NotI digested pPUB1 vector containing the polyubiquitin promoter, polyubiquitin intron with a KpnI-NotI-KpnI linker (5'CATTTGCGGCCGCAAATGGTAC3')(SEQ ID NO:20) insertion to create plasmid 1. The PAT selectable marker cassette (35S CAMV promoter, AdhI intron, phosphinothricin acetyl transferase gene (PAT), nos terminator) was excised from pIE108 (FIG. 14) and cloned into the HindIII site on plasmid 1 to give mononcot cassette E. Diagnostic restriction digestion was used to confirm that the selectable marker cassette was inserted 5' to 3' in the same orientation as the CTP2 EPSPS cassette.

A fragment containing the polyubiquitin promoter, polyubiquitin intron, CTP1 GOX and nos terminator was excised from cassette D with NoII and ligated into NotI cassette E to form monocot vector 1 (FIG. 14). Restriction digestion was used to confirm that the two cassettes were inserted in the same orientation.

The selectable marker cassette (35 CaMV promoter, AdhI intron, phosphinothricin acetyl transferase gene (PAT), nos) was excised from pIE108 and cloned into the Hind III site in 5) to give monocot cassette E.

Vector 1

A fragment containing the polyubiquitin promoter, polyubiquitin intron GOX and nos was exised from cassette D with NotI and cloned into NotI cut cassette E, to form monocot vector 1.

Vector 2 Cassette F

An EcoRI fragment from pUC4 (FIG. 15) containing the alcR cDNA and nos terminator sequences was blunt end-filled with DNA Polymerase I Klenow fragment, ligated into pUB1 with the KpnI-NotI-KpnI linker insertion and orientated by restriction analysis. The PAT selectable marker cassette was inserted in the HindIII site after excision from pIE108 and orientated by restriction analysis to create vector 1. Plasmid 1 above containing the polyubiquitin promoter, polyubiquitin intron, CTP2 EPSPS and nos terminator was cut with HindIII and a ΔHindIII-NotI-HindIII linker:

5'AGCTCGCAGCGGCCGCTGCA3' (SEQ ID NO: 22)
5'GCGTCGCCGGCGACGTTCGA3' (SEQ ID NO: 23)

inserted and orientated by sequencing to create vector 2.

A ClaI-NcoI-ClaI linker (5'CGATGCAGCCATGGCTGCAT3')(SEQ ID NO: 24) was inserted into pMF6 (FIG. 13) to give vector 3. An NcoI/KpnI fragment containing CTP1 GOX was excised from pDV1 and inserted into NcoI/KpnI cut vector 3 to create vector 4. A SalI fragment containing the maize AdhI intron, CTP1 GOX was excised from vector 4 and ligated into SalI cut pUC2 containing the alcA promoter and nos terminator and orientated by sequencing to create vector 5. A HindIII fragment from vector 5 containing the alcA promoter, maize AdhI intron, CTP1 GOX and nos terminator was ligated into HindIII cut vector 2 and orientated by restriction digestion. A NotI fragment from the resulting construct containing polyubiquitin promoter, polyubiquitin intron, CTP2 EPSPS, nos terminator, alcA promoter, maize AdhI intron, CTP1 GOX and nos terminator was ligated into Not1 cut vector 1 and orientated by restriction analysis to create monocot vector 2 (FIG. 16).

Example 4

Plant Transformation

Plasmids for dicot transformation were transferred to *Agrobacterium tumefaciens* LBA4404 using the freeze thaw method described by Holsters et al 1978.

Tobacco transformants were produced by the leaf disc method described by Bevan 1984. Shoots were regenerated on a medium containing 100 mg/l kanamycin. After rooting plants were transferred to the glasshouse and grown under 16 h light/8 h dark conditions.

Oilseed rape (*Brassica napus* cv westar) transformations were performed using the cotyledon petiole method described by Moloney et al 1989. Selection of transformed material was performed on kanamycin (15 mg/l). Rooted shoots were transferred directly to a soil based compost and grown to maturity under controlled glasshouse conditions (16 h day 20° C. day, 15° C. night 60% RH).

Maize transformation was performed using the particle bombardment approach as described by Klein et al 1988. Selections were performed on 1 mg/l biolophos.

Sugar beet transformation was performed using the guard cell protoplast procedure see our International Patent Publication No. WO95/10178.

Results showing details of the transgenic plants obtained are shown in Tables 2 and 3 below.

TABLE 2

Transformation Details For Tobacco

| Vector | Species | Shoots removed | Rooted |
|---|---|---|---|
| pDV1 | Tobacco | 150 | 57 |
| pDV2 | Tobacco | 150 | 60 |
| pDV3 | Tobacco | 270 | 77 |
| pDV4 | Tobacco | 350 | 135 |
| pDV5 | Tobacco | 150 | 75 |

TABLE 3

Transformation Details in Oil Seed Rape

| Vector | Species | Shooting Calli | Rooted |
|---|---|---|---|
| pDV1 | OSR | 14 | shoots from 14 |
| pDV2 | OSR | 13 | shoots from 13 |
| pDV3 | OSR | 18 | shoots from 18 |
| pDV4 | OSR | 20 | shoots from 20 |
| pDV5 | OSR | 19 | shoots from 18 |

Example 5

Transgenic Plant Analysis

Polymerase Chain Reaction (PCR)

Genomic DNA for PCR analysis of transgenic plants was prepared according to the s& method described by Edwards et at 1992. PCR was performed using conditions described by WL Jepson et at, Plant Molecular Biology Reporter, 9(2), 131–138 (1991). Primer sets were designed for each of the introduced cassettes.

The plants were analysed using the following oligonucleotide combinations:

pDV1 TMV1+GOX1, GOX3+nos1
pDV2 TMV1+EPSPS1, EPSPS3+nos1
pDV3 EPSPS3+GOX1
pDV4 35S+AlcR1, AlcA2+GOX1
pDV5 35S+AlcR1, AlcA2+GOX1, TMV1+EPSPS1

Oligonucleotide sequences are given below:

|  |  |  |
|---|---|---|
| TMV1 | 5'CTCGAGTATTTTTACAACAATTACCAACA | (SEQ ID NO:25) |
| GOX1 | 5'AATCAAGGTAACCTTGAATCCA | (SEQ ID NO:26) |
| GOX3 | 5'ACCACCAACGGTGTTCTTGCTGTTGA | (SEQ ID NO:27) |
| NOS1 | 5'GCATTACATGTTAATTATTACATGCTT | (SEQ ID NO:28) |
| EPSPS1 | 5'GTGATACGAGTTTCACCGCTAGCGAGAC | (SEQ ID NO:29) |
| EPSPS3 | 5'TACCTTGCGTGGACCAAAGACTCC | (SEQ ID NO:30) |
| 35S | 5'GTCAACATGGTGGAGCACG | (SEQ ID NO:31) |
| AlcR1 | 5'GTGAGAGTTTATGACTGGAGGCGCATCA | (SEQ ID NO:32) |
| AlcA2 | 5'GTCCGCACGGAGAGCCACAAACGA | (SEQ ID NO:33) |

Selection on Glyphosate

Kill Curves for Tobacco var *Samsun* and *Brassica napus* var Westar on glyphosate Both species were tested on a range of glyphosate concentrations by inserting, in the case of tobacco a 5–6 mm stem segment carrying a leaf node and in the case of oil seed rape the growing tip plus two leaves into MS medium containing glyphosate at 0, 0.0055, 0.011, 0.0275, 0.055 and 0.01 mM glyphosate isopropylamine salt. The results were scored after two weeks growth as and are given in Table 4 below.

TABLE 4

| Conc | Water | Tobacco |
|---|---|---|
| 0 | Good stem growth, 4–5 new leaves, roots up to 5 cm | As OSR |
| 0.005 | No stem growth, 1 new leaf, roots to 1 cm | No growth in any organ |
| 0.011 | No stem growth, no new leaves, roots ~ 0.5 cm | No growth in any organ |
| 0.0275 | No stem growth, no new leaves, roots ~ 2 mm | No growth in any organ |
| 0.055 | No growth in any organ, ends of stem blackened | No growth in any organ |

TABLE 4-continued

| Conc | Water | Tobacco |
| --- | --- | --- |
| 0.01 | As for 0.055 mM | No growth in any organ |

Selection for glyphosate tolerant transformants was performed on glyphosate concentrations of 0.01 and 0.05 mM.

Constitutively Tolerant Plants

Following from the data obtained on wild type plants, pDV1, 2 and 3 PCR+ve primary transformants were screened on MS medium containing glyphosate at the levels described above. For tobacco this was done by inserting three or four stem sections per transformant into the medium and using untransformed Samsun as control. Scoring was based on the behaviour of the majority. Plants showing tolerance at the higher concentration of herbicide were grown on to maturity in the glass house, for seed collection.

Segregation Test

Seeds were sterilized in 10% bleach for 10 min. After several washes in sterile water 200 seeds were sown on ½ MS medium (2.3 g/l MS salt, 1.5% sucrose, 0.8% Bactoagar, pH 5.9) containing 100 mg/l kanamycin. Seeds were grown at 26° C. with 16 hours/8 hours light/dark prior to scoring.

Western Analysis

Antibody Generation

GOX and EPSPS protein were over expressed in *E. Coli* using a pET expression system. Following IPTG induction GOX and EPSPS were electro eluted from the shake flask grown cell paste and used to immunise rabbits (two animals per clone).

Preparation of Tissue Extracts for Immunoblotting 120 mg of leaf tissue plus 60 mg PVPP and 500 µl extraction buffer (50 mM Tris-HCl pH 8, 1 mM EDTA, 0.3 mM DTT) were ground with a blender for several minutes. After homogenisation the extract was centrifuged at 15,000 rpm for 15 min. The supernatant was stored at −80° C. until required. Protein concentrations in the extract were measured according to Bradford.

SDS-PAGE and Immunoblotting

25 µg protein were separated by SDS-PAGE. The running buffer was 14.4% (w/v) glycine, 1% (w/v) SDS and 3% (w/v) Tris Base. The samples were loaded according to Laemmli.

After SDS-PAGE proteins were electroblotted overnight with 40 mA onto nitrocellulose (Hybond™ C, Amersham) using an electroblot unit from Biorad. The membrane was stained in 0.05% CPTS dissolved in 12 mM HCl. Blots were rinsed in 12 mM HCl and destained for 5–10 min in 0.5 M NaHCO$_3$ followed by an intensive rinse with H$_2$O. Membranes were then blocked, immunodetected and washed according to the Amersham ECL kit. Indirect immunodetections were performed with a 1:10000 dilution of a rabbit anti-GOX or anti-EPSPS polyclonal as first antibody and with a 1:1000 dilution of an anti-rabbit second antibody, associated with horseradish peroxidase. An additional wash was carried out overnight to eliminate background. Detection was performed using the ECL kit from Amersham and the results are shown in FIG. 22 in which Lane (1) is the control and the remaining lanes are transformants. The western analysis demonstrates that some transformants are capable of expressing GOX and EPSPS.

Constitutively Tolerant Plants

Cell extracts were prepared from each glyphosate tolerant plant and the amount of expresssed protein estimated by western analysis using antibody appropriate to the transformant. Plants expressing very high levels of GOX or EPSPS were tested on higher levels of glyphosate to relate level of expression to herbicide tolerance.

Inducibly Tolerant Plants

To demonstrate inducible tolerance to glyphosate PCR positive primary transformants from the transformations with pDV4 and 5 were transferred directly to the glass house. After two weeks the plants were induced by an ethanol root drench (5% solution) and left for 24 hours prior to western analysis performed to assess level of expression of GOX after induction. After a period of time to allow the plants to return to the uninduced state, the western analysis was repeated to allow selection of inducibly tolerant plants. Plants which showed the highest levels of GOX expression following ethanol treatment were taken forward to time course analysis. GOX levels were assessed at 6, 12, 18, 24, 36, 48 hours following ethanol treatment, by western analysis.

High expressing GOX plants for both pDV4 and pDV5 were used in glass house trials to demonstrate inducible glyphosate tolerance. Plants were induced using a range of ethanol concentrations (1–15%) by root drench application to pot grown plants. Following GOX induction plants were sprayed with glyphosate. Wild type controls and uninduced plants were also treated with herbicide.

Northern Analysis

Primary transformants containing dicots vector 2)., 3)., and 5). were analysed by northern blot analysis—using a CTP2 EPSPS probe as a NcoI Sac I fragment. Primary transformants containing the dicot vectors 1). 3). were analysed by northern blotting using a CTP1 GOX probe as a NcoI KpnI fragment. Similarly, transgenic corn lines containing monocot vectors 1). and 2). were analysed using a CTP2 EPSPS probe.

Transformants containing dicot vector 5). or monocot vector 2). were treated with a foliar application of 5% ethanol to induce GOX levels. RNA was isolated 24 hours after treatment and subjected to northern analysis with a CTP1 GOX probe.

Primary transformants which were PCR positive for the appropriate cassettes and showed GOX or EPSPS transcript levels were taken for further analysis.

Glyphosate Oxidoreductase Assay

Assays for glyphosate oxidoreductase were carried out as described by Kishore and Barry (WO 92/00377). These entailed measuring glyphosate—dependent uptake of oxygen using an oxygen electrode, detection of glyoxylate formation by reaction with 2,4-dinitrophenylhydrazine and determination of the hydrozone using HPLC or, preferably, using [$3-^{14}C$]-glyphosate as the substrate and detecting the formation of radioactive aminomethyl phosphonic acid via HPLC on an anion exchange column.

EPSPS Assay

Assays for 5-enol-pyruvylshikimate-3-phosphate (EPSP) synthase activity in plant extracts were carried out (1) by following the disappearance of the phosphoenol pyruvate substrate (as described by Rubin, J. L., Gaines, C. G and Jensen, R. A., in Plant Physiol (1984 75, 839–845) or (2) by conducting the assay in the reverse direction and coupling to pyruvate kinase and lactate dehydrogenase (as described by Mousdale D. M. and Coggins J. R. in Planta (1984) 160, 78–83) or (3) by using 14(-labelled phosphoenol pyruvate as substrate and detecting the formation of radioactive EPSP by HPLC on an anion exchange column and detecting using a flow-through radioactivity detector as described by Della-Cioppa et al in Proc. Nat. Acad. Sci. (USA) (1986), 83, 6873–6877. The latter assay was used to confirm that the EPSP synthase activity was, as expected, relatively resistant to inhibition by glyphosate.

What is claimed is:

1. A plant gene expression cassette comprising a first promoter operatively linked with a nucleotide sequence encoding the alcR protein, and an inducible promoter operatively linked to a glyphosate oxidase gene, said inducible promoter being activated by the alcR protein in the presence of a chemical inducer.

2. The plant gene expression cassette according to claim 1, wherein the inducible promoter is selected from the group consisting of alcA, alcR, aldA and a chimeric alcA/CaMV35 promoter.

3. A plant gene expression cassette comprising a promoter selected from the group consisting of alcA, alcR, aldR and a chimeric alcA/CaMV35 promoter operatively linked to a glyphosate oxidase gene.

4. The plant gene expression cassette according to claim 2 wherein the inducible promoter is a chimeric promoter.

5. A plant cell containing a plant expression cassette according to claim 3.

6. The plant cell according to claim 5, wherein the plant gene expression cassette is stably incorporated in the plant's genome.

7. A plant tissue comprising the plant cell according to claim 5.

8. A method of controlling herbicide resistance comprising transforming a plant cell with the plant gene expression cassette of claim 3.

9. A plant gene expression cassette comprising a first promoter operatively linked to a first target gene which codes for a 5-enol-pyruvylshikimate 3-phosphonate synthase; and a second inducible promoter operatively linked to a second target gene coding for a glyphosate oxidase, said second inducible promoter being activated by the alcR protein in the presence of a chemical inducer.

10. The gene expression cassette according to claim 9 wherein the first promoter is a constitutive promoter.

11. A plant cell containing a plant gene expression cassette according to claim 1.

12. A plant cell containing a plant gene expression cassette according to claim 9.

13. A plant containing a plant gene expression cassette according to claim 3.

14. A plant containing a plant gene expression cassette according to claim 1.

15. A plant containing a plant gene expression cassette according to claim 9.

16. A method of controlling herbicide resistance comprising transforming a plant cell with the plant gene expression cassette of claim 1.

17. A method of controlling herbicide resistance comprising transforming a plant cell with the plant gene expression cassette of claim 9.

18. A method of controlling weeds in a field of plants, wherein said field of plants is comprised of plants of claim 13, 14 or 15, comprising applying to said field a weed controlling amount of the herbicide N-phosphonomethylglycine and an activating amount of a chemical inducer whereby application of the chemical inducer causes expression of glyphosate oxidase.

19. The method of claim 18 wherein said chemical inducer is an alcohol or ketone.

20. The method of claim 19 wherein said chemical inducer is ethanol.

* * * * *

SEQUENCE LISTING

<160> NUMBER OF SEQ ID NOS: 33

<210> SEQ ID NO 1
<211> LENGTH: 509
<212> TYPE: DNA
<213> ORGANISM: Arabidopsis sp.
<220> FEATURE:
<221> NAME/KEY: CDS
<222> LOCATION: (1)..(507)

<400> SEQUENCE: 1

```
aag ctt acc atg gct tcc tct atg ctc tct t cc gct act atg gtt gcc     48
Lys Leu Thr Met Ala Ser Ser Met Leu Ser S er Ala Thr Met Val Ala
1               5                   10                  15 tct ccg gct cag gcc act atg gtc gct cct t tc aac gga ctt aag tcc     96
Ser Pro Ala Gln Ala Thr Met Val Ala Pro P he Asn Gly Leu Lys Ser
            20                  25                  30 tcc gct gcc ttc cca gcc acc cgc aag gct a ac aac gac att act tcc    144
Ser Ala Ala Phe Pro Ala Thr Arg Lys Ala A sn Asn Asp Ile Thr Ser
        35                  40                  45 atc aca agc aac ggc gga aga gtt aac tgt a tg cag gtg tgg cct ccg    192
Ile Thr Ser Asn Gly Gly Arg Val Asn Cys M et Gln Val Trp Pro Pro
 50                  55                  60 att gga aag aag aag ttt gag act ctc tct t ac ctt cct gac ctt acc    240
Ile Gly Lys Lys Lys Phe Glu Thr Leu Ser T yr Leu Pro Asp Leu Thr
65                  70                  75                  80 gat tcc ggt ggt cgc gtc aac tgt atg cag g ct atg gct gag aac cac    288
Asp Ser Gly Gly Arg Val Asn Cys Met Gln A la Met Ala Glu Asn His
                85                  90                  95 aag aag gtt ggt atc gct gga gct gga atc g tt ggt gtt tgc act gct    336
Lys Lys Val Gly Ile Ala Gly Ala Gly Ile V al Gly Val Cys Thr Ala
            100                 105                 110 ttg atg ctt caa cgt cgt gga ttc aag gtt a cc ttg att gat cca aac    384
Leu Met Leu Gln Arg Arg Gly Phe Lys Val T hr Leu Ile Asp Pro Asn
        115                 120                 125 cca cca ggt gaa ggt gct tct ttc ggt aac g ct ggt tgc ttc aac ggt    432
Pro Pro Gly Glu Gly Ala Ser Phe Gly Asn A la Gly Cys Phe Asn Gly
    130                 135                 140 tcc tcc gtt gtt cca atg tcc atg cca gga a ac ttg act agc gtt cca    480
Ser Ser Val Val Pro Met Ser Met Pro Gly A sn Leu Thr Ser Val Pro
145                 150                 155                 160 aag tgg ctt ctg gat cct gtt gtg aat tc                              509
Lys Trp Leu Leu Asp Pro Val Val Asn
                165
```

<210> SEQ ID NO 2
<211> LENGTH: 169
<212> TYPE: PRT
<213> ORGANISM: Arabidopsis sp.

<400> SEQUENCE: 2

```
Lys Leu Thr Met Ala Ser Ser Met Leu Ser S er Ala Thr Met Val Ala
1               5                   10                  15

Ser Pro Ala Gln Ala Thr Met Val Ala Pro P he Asn Gly Leu Lys Ser
            20                  25                  30
```

```
Ser Ala Ala Phe Pro Ala Thr Arg Lys Ala Asn Asn Asp Ile Thr Ser
         35                  40                  45

Ile Thr Ser Asn Gly Gly Arg Val Asn Cys Met Gln Val Trp Pro Pro
 50                  55                  60

Ile Gly Lys Lys Lys Phe Glu Thr Leu Ser Tyr Leu Pro Asp Leu Thr
 65                  70                  75                  80

Asp Ser Gly Gly Arg Val Asn Cys Met Gln Ala Met Ala Glu Asn His
                 85                  90                  95

Lys Lys Val Gly Ile Ala Gly Ile Val Gly Val Cys Thr Ala
                100                 105                 110

Leu Met Leu Gln Arg Arg Gly Phe Lys Val Thr Leu Ile Asp Pro Asn
         115                 120                 125

Pro Pro Gly Glu Gly Ala Ser Phe Gly Asn Ala Gly Cys Phe Asn Gly
     130                 135                 140

Ser Ser Val Val Pro Met Ser Met Pro Gly Asn Leu Thr Ser Val Pro
145                 150                 155                 160

Lys Trp Leu Leu Asp Pro Val Val Asn
                165

<210> SEQ ID NO 3
<211> LENGTH: 553
<212> TYPE: DNA
<213> ORGANISM: Arabidopsis sp.
<220> FEATURE:
<221> NAME/KEY: CDS
<222> LOCATION: (1)..(549)

<400> SEQUENCE: 3 aag ctt acg gat cca atg ggt cca ttg tcc atc cgt ttc agc tac ttt    48
Lys Leu Thr Asp Pro Met Gly Pro Leu Ser Ile Arg Phe Ser Tyr Phe
  1               5                  10                  15 cca acc atc atg cct tgg ttg att cgt ttc ttg ctt gct gga aga cca    96
Pro Thr Ile Met Pro Trp Leu Ile Arg Phe Leu Leu Ala Gly Arg Pro
                 20                  25                  30 aac aag gtg aag gag caa gct aag gca ctc cgt aac ctc atc aag tcc   144
Asn Lys Val Lys Glu Gln Ala Lys Ala Leu Arg Asn Leu Ile Lys Ser
             35                  40                  45 act gtg cct ttg atc aag tcc ttg gct gag gag gct gat gct agc cac   192
Thr Val Pro Leu Ile Lys Ser Leu Ala Glu Glu Ala Asp Ala Ser His
 50                  55                  60 ctt atc cgt cac gaa ggt cac ctt acc gtg tac cgt gga gaa gca gac   240
Leu Ile Arg His Glu Gly His Leu Thr Val Tyr Arg Gly Glu Ala Asp
 65                  70                  75                  80 ttc gcc aag gac cgt gga ggt tgg gaa ctt cgt cgt ctc aac ggt gtt   288
Phe Ala Lys Asp Arg Gly Gly Trp Glu Leu Arg Arg Leu Asn Gly Val
                 85                  90                  95 cgt act caa atc ctc agc gct gat gca ttg cgt gat ttc gat cct aac   336
Arg Thr Gln Ile Leu Ser Ala Asp Ala Leu Arg Asp Phe Asp Pro Asn
            100                 105                 110 ttg tct cac gcc ttt acc aag gga atc ctt atc gaa gag aac ggt cac   384
Leu Ser His Ala Phe Thr Lys Gly Ile Leu Ile Glu Glu Asn Gly His
        115                 120                 125 acc atc aac cca caa ggt ctc gtg act ctc ttg ttt cgt cgt ttc atc   432
Thr Ile Asn Pro Gln Gly Leu Val Thr Leu Leu Phe Arg Arg Phe Ile
130                 135                 140 gct aac ggt gga gag ttc gtg tct gct cgt gtt atc gga ttc gag act   480
Ala Asn Gly Gly Glu Phe Val Ser Ala Arg Val Ile Gly Phe Glu Thr
145                 150                 155                 160 gaa ggt cgt gct ctc aag ggt atc acc acc acc aac ggt gtt ctt gct   528
```

```
Glu Gly Arg Ala Leu Lys Gly Ile Thr Thr Thr Asn Gly Val Leu Ala
                165                 170                 175 gtt gat gct gca gtg ttg tga attc                                          553
Val Asp Ala Ala Val Leu
        180

<210> SEQ ID NO 4
<211> LENGTH: 182
<212> TYPE: PRT
<213> ORGANISM: Arabidopsis sp.

<400> SEQUENCE: 4

Lys Leu Thr Asp Pro Met Gly Pro Leu Ser Ile Arg Phe Ser Tyr Phe
  1               5                  10                  15

Pro Thr Ile Met Pro Trp Leu Ile Arg Phe Leu Leu Ala Gly Arg Pro
                 20                  25                  30

Asn Lys Val Lys Glu Gln Ala Lys Ala Leu Arg Asn Leu Ile Lys Ser
             35                  40                  45

Thr Val Pro Leu Ile Lys Ser Leu Ala Glu Glu Ala Asp Ala Ser His
         50                  55                  60

Leu Ile Arg His Glu Gly His Leu Thr Val Tyr Arg Gly Glu Ala Asp
 65                  70                  75                  80

Phe Ala Lys Asp Arg Gly Gly Trp Glu Leu Arg Arg Leu Asn Gly Val
                 85                  90                  95

Arg Thr Gln Ile Leu Ser Ala Asp Ala Leu Arg Asp Phe Asp Pro Asn
            100                 105                 110

Leu Ser His Ala Phe Thr Lys Gly Ile Leu Ile Glu Glu Asn Gly His
        115                 120                 125

Thr Ile Asn Pro Gln Gly Leu Val Thr Leu Leu Phe Arg Arg Phe Ile
    130                 135                 140

Ala Asn Gly Gly Glu Phe Val Ser Ala Arg Val Ile Gly Phe Glu Thr
145                 150                 155                 160

Glu Gly Arg Ala Leu Lys Gly Ile Thr Thr Thr Asn Gly Val Leu Ala
                165                 170                 175

Val Asp Ala Ala Val Leu
        180

<210> SEQ ID NO 5
<211> LENGTH: 570
<212> TYPE: DNA
<213> ORGANISM: Arabidopsis sp.
<220> FEATURE:
<221> NAME/KEY: CDS
<222> LOCATION: (1)..(570)

<400> SEQUENCE: 5 aag ctt act gca gtt gtt gca gct ggt gca cac tcc aag tct ctt gct         48
Lys Leu Thr Ala Val Val Ala Ala Gly Ala His Ser Lys Ser Leu Ala
  1               5                  10                  15 aac tcc ctt ggt gat gac atc cca ttg gat acc gaa cgt gga tac cac         96
Asn Ser Leu Gly Asp Asp Ile Pro Leu Asp Thr Glu Arg Gly Tyr His
                 20                  25                  30 atc gtg atc gcc aac cca gaa gct gct cca cgt att cca act acc gat        144
Ile Val Ile Ala Asn Pro Glu Ala Ala Pro Arg Ile Pro Thr Thr Asp
             35                  40                  45 gct tct gga aag ttc atc gct act cct atg gag atg ggt ctt cgt gtt        192
Ala Ser Gly Lys Phe Ile Ala Thr Pro Met Glu Met Gly Leu Arg Val
         50                  55                  60 gct gga acc gtt gag ttc gct ggt ctc act gct gct cct aac tgg aag        240
```

```
Ala Gly Thr Val Glu Phe Ala Gly Leu Thr A la Ala Pro Asn Trp Lys
 65                  70                  75                  80 cgt gct cac gtt ctc tac act cgt gct cgt a ag ttg ctt cca gct ctc      288
Arg Ala His Val Leu Tyr Thr Arg Ala Arg L ys Leu Leu Pro Ala Leu
                     85                  90                  95 gct cct gcc agt tct gaa gaa cgt tac tcc a ag tgg atg ggt ttc cgt      336
Ala Pro Ala Ser Ser Glu Glu Arg Tyr Ser L ys Trp Met Gly Phe Arg
                 100                 105                 110 cca agc atc cca gat tcc ctt cca gtg att g gt cgt gct acc cgt act      384
Pro Ser Ile Pro Asp Ser Leu Pro Val Ile G ly Arg Ala Thr Arg Thr
             115                 120                 125 cca gac gtt atc tac gct ttc ggt cac ggt c ac ctc ggt atg act ggt      432
Pro Asp Val Ile Tyr Ala Phe Gly His Gly H is Leu Gly Met Thr Gly
         130                 135                 140 gct cca atg acc gca acc ctc gtt tct gag c tc ctc gca ggt gag aag      480
Ala Pro Met Thr Ala Thr Leu Val Ser Glu L eu Leu Ala Gly Glu Lys
145                 150                 155                 160 acc tct atc gac atc tct cca ttc gca cca a ac cgt ttc ggt att ggt      528
Thr Ser Ile Asp Ile Ser Pro Phe Ala Pro A sn Arg Phe Gly Ile Gly
                 165                 170                 175 aag tcc aag caa act ggt cct gca tcc taa g gt acc gaa ttc              570
Lys Ser Lys Gln Thr Gly Pro Ala Ser     Gly Thr Glu Phe
             180                 185

<210> SEQ ID NO 6
<211> LENGTH: 185
<212> TYPE: PRT
<213> ORGANISM: Arabidopsis sp.

<400> SEQUENCE: 6

Lys Leu Thr Ala Val Ala Ala Gly Ala H is Ser Lys Ser Leu Ala
 1               5                  10                  15

Asn Ser Leu Gly Asp Asp Ile Pro Leu Asp T hr Glu Arg Gly Tyr His
                 20                  25                  30

Ile Val Ile Ala Asn Pro Glu Ala Ala Pro A rg Ile Pro Thr Thr Asp
             35                  40                  45

Ala Ser Gly Lys Phe Ile Ala Thr Pro Met G lu Met Gly Leu Arg Val
         50                  55                  60

Ala Gly Thr Val Glu Phe Ala Gly Leu Thr A la Ala Pro Asn Trp Lys
 65                  70                  75                  80

Arg Ala His Val Leu Tyr Thr Arg Ala Arg L ys Leu Leu Pro Ala Leu
                     85                  90                  95

Ala Pro Ala Ser Ser Glu Glu Arg Tyr Ser L ys Trp Met Gly Phe Arg
                 100                 105                 110

Pro Ser Ile Pro Asp Ser Leu Pro Val Ile G ly Arg Ala Thr Arg Thr
             115                 120                 125

Pro Asp Val Ile Tyr Ala Phe Gly His Gly H is Leu Gly Met Thr Gly
         130                 135                 140

Ala Pro Met Thr Ala Thr Leu Val Ser Glu L eu Leu Ala Gly Glu Lys
145                 150                 155                 160

Thr Ser Ile Asp Ile Ser Pro Phe Ala Pro A sn Arg Phe Gly Ile Gly
                 165                 170                 175

Lys Ser Lys Gln Thr Gly Pro Ala Ser
             180                 185

<210> SEQ ID NO 7
<211> LENGTH: 4
<212> TYPE: PRT
```

<213> ORGANISM: Arabidopsis sp.

<400> SEQUENCE: 7

Gly Thr Glu Phe
1

<210> SEQ ID NO 8
<211> LENGTH: 1138
<212> TYPE: DNA
<213> ORGANISM: Artificial
<220> FEATURE:
<223> OTHER INFORMATION: Plasmid pMJB1

<400> SEQUENCE: 8

| aagcttgcat | gcctgcaggt | caacatggtg | gagcacgaca | cacttgtcta | c tccaaaaat | 60 |
| atcaaagata | cagtctcaga | agaccaaagg | gcaattgaga | cttttcaaca | a agggtaata | 120 |
| tccggaaacc | tcctcggatt | ccattgccca | gctatctgtc | actttattgt | g aagatagtg | 180 |
| gaaaggaag | gtggctccta | caaatgccat | cattgcgata | aaggaaaggc | c atcgttgaa | 240 |
| gatgcctctg | ccgacagtgg | tcccaaagat | ggaccccac | ccacgaggag | c atcgtggaa | 300 |
| aaagaagac | gttccaacca | cgtcttcaaa | gcaagtggat | tgatgtgata | a catggtgga | 360 |
| gcacgacaca | cttgtctact | ccaaaaatat | caaagataca | gtctcagaag | a ccaaagggc | 420 |
| aattgagact | tttcaacaaa | gggtaatatc | cggaaacctc | ctcggattcc | a ttgcccagc | 480 |
| tatctgtcac | tttattgtga | agatagtgga | aaggaaggt | ggctcctaca | a atgccatca | 540 |
| ttgcgataaa | ggaaaggcca | tcgttgaaga | tgcctctgcc | gacagtggtc | c caagatgg | 600 |
| accccaccc | acgaggagca | tcgtggaaaa | agaagacgtt | ccaaccacg t | cttcaaagc | 660 |
| aagtggattg | atgtgatatc | tccactgacg | taagggatga | cgcacaatcc | c actatcctt | 720 |
| cgcaagaccc | ttcctctata | taaggaagtt | catttcattt | ggagaggacc | t cgagtattt | 780 |
| ttacaacaat | taccaacaac | aacaaacaac | aaacaacatt | acaattacta | t ttacaatta | 840 |
| caccatggat | ccccgggtac | cgagctcgaa | ttttcccgat | cgttcaaaca | t ttggcaata | 900 |
| aagtttctta | agattgaatc | ctgttgccgg | tcttgcgatg | attatcatat | a atttctgtt | 960 |
| gaattacgtt | aagcatgtaa | taattaacat | gtaatgcatg | acgttattta | t gagatgggt | 1020 |
| ttttatgatt | agagtcccgc | aattatacat | ttaatacgcg | atagaaaaca | a aatatagcg | 1080 |
| cgcaaactag | gataaattat | cgcgcgcggt | gtcatctatg | ttactagatc | g ggaattc | 1138 |

<210> SEQ ID NO 9
<211> LENGTH: 1138
<212> TYPE: DNA
<213> ORGANISM: Artificial
<220> FEATURE:
<223> OTHER INFORMATION: Plasmid pMJB1

<400> SEQUENCE: 9

| gaattcccga | tctagtaaca | tagatgacac | cgcgcgcgat | aatttatcct | a gtttgcgcg | 60 |
| ctatattttg | ttttctatcg | cgtattaaat | gtataattgc | gggactctaa | t cataaaaac | 120 |
| ccatctcata | aataacgtca | tgcattacat | gttaattatt | acatgcttaa | c gtaattcaa | 180 |
| cagaaattat | atgataatca | tcgcaagacc | ggcaacagga | ttcaatctta | a gaaacttta | 240 |
| ttgccaaatg | tttgaacgat | cggggaaatt | cgagctcggt | acccggggat | c catggtgta | 300 |
| attgtaaata | gtaattgtaa | tgttgtttgt | tgtttgttgt | tgttggtaat | t gttgtaaaa | 360 |
| atactcgagg | tcctctccaa | atgaaatgaa | cttccttata | tagaggaagg | g tcttgcgaa | 420 |

```
ggatagtggg attgtgcgtc atcccttacg tcagtggaga tatcacatca a tccacttgc      480 tttgaagacg tggttggaac gtcttctttt ttccacgatg ctcctcgtgg g tggggtcc      540 atctttggga ccactgtcgg cagaggcatc ttcaacgatg gcctttcctt t atcgcaatg    600 atggcatttg taggagccac cttccttttc cactatcttc acaataaagt g acagatagc    660 tgggcaatgg aatccgagga ggtttccgga tattacccttt tgttgaaaag t ctcaattgc   720 cctttggtct tctgagactg tatctttgat attttttggag tagacaagtg t gtcgtgctc   780 caccatgtta tcacatcaat ccacttgctt tgaagacgtg gttggaacgt c ttcttttt    840 ccacgatgct cctcgtgggt ggggtccat cttttgggacc actgtcggca g aggcatctt   900 caacgatggc cttccttta tcgcaatgat ggcatttgta ggagccacct t ccttttcca   960 ctatcttcac aataaagtga cagatagctg ggcaatggaa tccgaggagg t ttccggata  1020 ttaccctttg ttgaaaagtc tcaattgccc tttggtcttc tgagactgta t ctttgatat  1080 ttttggagta gacaagtgtg tcgtgctcca ccatgttgac ctgcaggcat g caagctt    1138
```

```
<210> SEQ ID NO 10
<211> LENGTH: 460
<212> TYPE: DNA
<213> ORGANISM: Petunia hybrida
<220> FEATURE:
<221> NAME/KEY: CDS
<222> LOCATION: (1)..(456)

<400> SEQUENCE: 10
```

```
aag ctt acc atg gct caa gtt agc aga atc t gc aat ggt gtg cag aac        48
Lys Leu Thr Met Ala Gln Val Ser Arg Ile C ys Asn Gly Val Gln Asn
1               5                  10                 15 cca tct ctt atc tcc aat ctc tcg aaa tcc a gt caa cgc aaa tct ccc        96
Pro Ser Leu Ile Ser Asn Leu Ser Lys Ser S er Gln Arg Lys Ser Pro
            20                  25                 30 tta tcg gtt tct ctg aag acg cag cag cat c ca cga gct tat ccg att       144
Leu Ser Val Ser Leu Lys Thr Gln Gln His P ro Arg Ala Tyr Pro Ile
        35                  40                 45 tcg tcg tcg tgg gga ttg aag aag agt ggg a tg acg tta att ggc tct       192
Ser Ser Ser Trp Gly Leu Lys Lys Ser Gly M et Thr Leu Ile Gly Ser
    50                  55                  60 gag ctt cgt cct ctt aag gtc atg tct tct g tt tcc acg gcg tgt atg       240
Glu Leu Arg Pro Leu Lys Val Met Ser Ser V al Ser Thr Ala Cys Met
65                  70                  75                  80 ctt cac ggt gca agc agc cgt cca gca act g ct cgt aag tcc tct ggt       288
Leu His Gly Ala Ser Ser Arg Pro Ala Thr A la Arg Lys Ser Ser Gly
                85                  90                  95 ctt tct gga acc gtc cgt att cca ggt gac a ag tct atc tcc cac agg       336
Leu Ser Gly Thr Val Arg Ile Pro Gly Asp L ys Ser Ile Ser His Arg
            100                 105                110 tcc ttc atg ttt gga ggt ctc gct agc ggt g aa act cgt atc acc ggt       384
Ser Phe Met Phe Gly Gly Leu Ala Ser Gly G lu Thr Arg Ile Thr Gly
        115                 120                125 ctt ttg gaa ggt gaa gat gtt atc aac act g gt aag gct atg caa gct       432
Leu Leu Glu Gly Glu Asp Val Ile Asn Thr G ly Lys Ala Met Gln Ala
    130                 135                140 atg ggt gcc agg atc ctg ttg tga attc                                    460
Met Gly Ala Arg Ile Leu Leu
145                 150
```

```
<210> SEQ ID NO 11
<211> LENGTH: 151
```

-continued

```
<212> TYPE: PRT
<213> ORGANISM: Petunia hybrida

<400> SEQUENCE: 11

Lys Leu Thr Met Ala Gln Val Ser Arg Ile C ys Asn Gly Val Gln Asn
1               5                   10                  15

Pro Ser Leu Ile Ser Asn Leu Ser Lys Ser S er Gln Arg Lys Ser Pro
            20                  25                  30

Leu Ser Val Ser Leu Lys Thr Gln Gln His P ro Arg Ala Tyr Pro Ile
        35                  40                  45

Ser Ser Ser Trp Gly Leu Lys Lys Ser Gly M et Thr Leu Ile Gly Ser
    50                  55                  60

Glu Leu Arg Pro Leu Lys Val Met Ser Ser V al Ser Thr Ala Cys Met
65                  70                  75                  80

Leu His Gly Ala Ser Ser Arg Pro Ala Thr A la Arg Lys Ser Ser Gly
                85                  90                  95

Leu Ser Gly Thr Val Arg Ile Pro Gly Asp L ys Ser Ile Ser His Arg
            100                 105                 110

Ser Phe Met Phe Gly Gly Leu Ala Ser Gly G lu Thr Arg Ile Thr Gly
        115                 120                 125

Leu Leu Glu Gly Glu Asp Val Ile Asn Thr G ly Lys Ala Met Gln Ala
    130                 135                 140

Met Gly Ala Arg Ile Leu Leu
145                 150

<210> SEQ ID NO 12
<211> LENGTH: 660
<212> TYPE: DNA
<213> ORGANISM: Petunia hybrida
<220> FEATURE:
<221> NAME/KEY: CDS
<222> LOCATION: (1)..(660)

<400> SEQUENCE: 12 aag ctt agg atc cgt aag gaa ggt gat act t gg atc att gat ggt gtt      48
Lys Leu Arg Ile Arg Lys Glu Gly Asp Thr T rp Ile Ile Asp Gly Val
1               5                   10                  15 ggt aac ggt gga ctc ctt gct cct gag gct c ct ctc gat ttc ggt aac      96
Gly Asn Gly Gly Leu Leu Ala Pro Glu Ala P ro Leu Asp Phe Gly Asn
            20                  25                  30 gct gca act ggt tgc cgt ttg act atg ggt c tt gtt ggt gtt tac gat     144
Ala Ala Thr Gly Cys Arg Leu Thr Met Gly L eu Val Gly Val Tyr Asp
        35                  40                  45 ttc gat agc act ttc att ggt gac gct tct c tc act aag cgt cca atg     192
Phe Asp Ser Thr Phe Ile Gly Asp Ala Ser L eu Thr Lys Arg Pro Met
    50                  55                  60 ggt cgt gtg ttg aac cca ctt cgc gaa atg g gt gtg cag gtg aag tct     240
Gly Arg Val Leu Asn Pro Leu Arg Glu Met G ly Val Gln Val Lys Ser
65                  70                  75                  80 gaa gac ggt gat cgt ctt cca gtt acc ttg c gt gga cca aag act cca     288
Glu Asp Gly Asp Arg Leu Pro Val Thr Leu A rg Gly Pro Lys Thr Pro
                85                  90                  95 acg cca atc acc tac agg gta cct atg gct t cc gct caa gtg aag tcc     336
Thr Pro Ile Thr Tyr Arg Val Pro Met Ala S er Ala Gln Val Lys Ser
            100                 105                 110 gct gtt ctg ctt gct ggt ctc aac acc cca g gt atc acc act gtt atc     384
Ala Val Leu Leu Ala Gly Leu Asn Thr Pro G ly Ile Thr Thr Val Ile
        115                 120                 125 gag cca atc atg act cgt gac cac act gaa a ag atg ctt caa ggt ttt     432
```

```
                                                                                          480
Glu Pro Ile Met Thr Arg Asp His Thr Glu Lys Met Leu Gln Gly Phe
    130                 135                 140
ggt gct aac ctt acc gtt gag act gat gct gac ggt gtg cgt acc atc            480
Gly Ala Asn Leu Thr Val Glu Thr Asp Ala Asp Gly Val Arg Thr Ile
145                 150                 155                 160
cgt ctt gaa ggt cgt ggt aag ctc acc ggt caa gtg att gat gtt cca            528
Arg Leu Glu Gly Arg Gly Lys Leu Thr Gly Gln Val Ile Asp Val Pro
                165                 170                 175
ggt gat cca tcc tct act gct ttc cca ttg gtt gct gcc ttg ctt gtt            576
Gly Asp Pro Ser Ser Thr Ala Phe Pro Leu Val Ala Ala Leu Leu Val
                180                 185                 190
cca ggt tcc gac gtc acc atc ctt aac gtt ttg atg aac cca acc cgt            624
Pro Gly Ser Asp Val Thr Ile Leu Asn Val Leu Met Asn Pro Thr Arg
                195                 200                 205
act ggt ctc atc ttg act ctg cag tgt tgt gaa ttc                            660
Thr Gly Leu Ile Leu Thr Leu Gln Cys Cys Glu Phe
    210                 215                 220

<210> SEQ ID NO 13
<211> LENGTH: 220
<212> TYPE: PRT
<213> ORGANISM: Petunia hybrida

<400> SEQUENCE: 13

Lys Leu Arg Ile Arg Lys Glu Gly Asp Thr Trp Ile Ile Asp Gly Val
1               5                   10                  15

Gly Asn Gly Gly Leu Leu Ala Pro Glu Ala Pro Leu Asp Phe Gly Asn
                20                  25                  30

Ala Ala Thr Gly Cys Arg Leu Thr Met Gly Leu Val Gly Val Tyr Asp
            35                  40                  45

Phe Asp Ser Thr Phe Ile Gly Asp Ala Ser Leu Thr Lys Arg Pro Met
        50                  55                  60

Gly Arg Val Leu Asn Pro Leu Arg Glu Met Gly Val Gln Val Lys Ser
65                  70                  75                  80

Glu Asp Gly Asp Arg Leu Pro Val Thr Leu Arg Gly Pro Lys Thr Pro
                85                  90                  95

Thr Pro Ile Thr Tyr Arg Val Pro Met Ala Ser Ala Gln Val Lys Ser
                100                 105                 110

Ala Val Leu Leu Ala Gly Leu Asn Thr Pro Gly Ile Thr Thr Val Ile
            115                 120                 125

Glu Pro Ile Met Thr Arg Asp His Thr Glu Lys Met Leu Gln Gly Phe
    130                 135                 140

Gly Ala Asn Leu Thr Val Glu Thr Asp Ala Asp Gly Val Arg Thr Ile
145                 150                 155                 160

Arg Leu Glu Gly Arg Gly Lys Leu Thr Gly Gln Val Ile Asp Val Pro
                165                 170                 175

Gly Asp Pro Ser Ser Thr Ala Phe Pro Leu Val Ala Ala Leu Leu Val
                180                 185                 190

Pro Gly Ser Asp Val Thr Ile Leu Asn Val Leu Met Asn Pro Thr Arg
                195                 200                 205

Thr Gly Leu Ile Leu Thr Leu Gln Cys Cys Glu Phe
    210                 215                 220

<210> SEQ ID NO 14
<211> LENGTH: 547
<212> TYPE: DNA
<213> ORGANISM: Petunia hybrida
<220> FEATURE:
```

<221> NAME/KEY: CDS
<222> LOCATION: (1)..(534)

<400> SEQUENCE: 14

| | | | | | | | | | | | | | | | | |
|---|---|---|---|---|---|---|---|---|---|---|---|---|---|---|---|---|
| aag | ctt | ctg | cag | gaa | atg | ggt | gcc | gac | atc | g aa | gtg | atc | aac | cca | cgt | 48 |
| Lys | Leu | Leu | Gln | Glu | Met | Gly | Ala | Asp | Ile | G lu | Val | Ile | Asn | Pro | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ctt | gct | ggt | gga | gaa | gac | gtg | gct | gac | ttg | c gt | gtt | cgt | tct | tct | act | 96 |
| Leu | Ala | Gly | Gly | Glu | Asp | Val | Ala | Asp | Leu | A rg | Val | Arg | Ser | Ser | Thr | |
| | | | 20 | | | | | 25 | | | | | 30 | | | |

| | | | | | | | | | | | | | | | | |
|---|---|---|---|---|---|---|---|---|---|---|---|---|---|---|---|---|
| ttg | aag | ggt | gtt | act | gtt | cca | gaa | gac | cgt | g ct | cct | tct | atg | atc | gac | 144 |
| Leu | Lys | Gly | Val | Thr | Val | Pro | Glu | Asp | Arg | A la | Pro | Ser | Met | Ile | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| gag | tat | cca | att | ctc | gct | gtt | gca | gct | gca | t tc | gct | gaa | ggt | gct | acc | 192 |
| Glu | Tyr | Pro | Ile | Leu | Ala | Val | Ala | Ala | Ala | P he | Ala | Glu | Gly | Ala | Thr | |
| 50 | | | | | 55 | | | | | 60 | | | | | | |

| | | | | | | | | | | | | | | | | |
|---|---|---|---|---|---|---|---|---|---|---|---|---|---|---|---|---|
| gtt | atg | aac | ggt | ttg | gaa | gaa | ctc | cgt | gtt | a ag | gaa | agc | gac | cgt | ctt | 240 |
| Val | Met | Asn | Gly | Leu | Glu | Glu | Leu | Arg | Val | L ys | Glu | Ser | Asp | Arg | Leu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| tct | gct | gtc | gca | aac | ggt | ctc | aag | ctc | aac | g gt | gtt | gat | tgc | gat | gaa | 288 |
| Ser | Ala | Val | Ala | Asn | Gly | Leu | Lys | Leu | Asn | G ly | Val | Asp | Cys | Asp | Glu | |
| | | | | 85 | | | | | 90 | | | | | 95 | | |

| | | | | | | | | | | | | | | | | |
|---|---|---|---|---|---|---|---|---|---|---|---|---|---|---|---|---|
| ggt | gag | act | tct | ctc | gtc | gtg | cgt | ggt | cgt | c ct | gac | ggt | aag | ggt | ctc | 336 |
| Gly | Glu | Thr | Ser | Leu | Val | Val | Arg | Gly | Arg | P ro | Asp | Gly | Lys | Gly | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| ggt | aac | gct | tct | gga | gca | gct | gtc | gct | acc | c ac | ctc | gat | cac | cgt | atc | 384 |
| Gly | Asn | Ala | Ser | Gly | Ala | Ala | Val | Ala | Thr | H is | Leu | Asp | His | Arg | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| gct | atg | agc | ttc | ctc | gtt | atg | ggt | ctc | gtt | t ct | gaa | aac | cct | gtt | act | 432 |
| Ala | Met | Ser | Phe | Leu | Val | Met | Gly | Leu | Val | S er | Glu | Asn | Pro | Val | Thr | |
| 130 | | | | | 135 | | | | | 140 | | | | | | |

| | | | | | | | | | | | | | | | | |
|---|---|---|---|---|---|---|---|---|---|---|---|---|---|---|---|---|
| gtt | gat | gat | gct | act | atg | atc | gct | act | agc | t tc | cca | gag | ttc | atg | gat | 480 |
| Val | Asp | Asp | Ala | Thr | Met | Ile | Ala | Thr | Ser | P he | Pro | Glu | Phe | Met | Asp | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ttg | atg | gct | ggt | ctt | gga | gct | aag | atc | gaa | c tc | tcc | gac | act | aag | gct | 528 |
| Leu | Met | Ala | Gly | Leu | Gly | Ala | Lys | Ile | Glu | L eu | Ser | Asp | Thr | Lys | Ala | |
| | | | 165 | | | | | 170 | | | | | 175 | | | |

| | | | | |
|---|---|---|---|---|
| gct | tga | tgagctcgaa | ttc | 547 |
| Ala | | | | |

<210> SEQ ID NO 15
<211> LENGTH: 177
<212> TYPE: PRT
<213> ORGANISM: Petunia hybrida

<400> SEQUENCE: 15

Lys Leu Leu Gln Glu Met Gly Ala Asp Ile G lu Val Ile Asn Pro Arg
1               5                   10                  15

Leu Ala Gly Gly Glu Asp Val Ala Asp Leu A rg Val Arg Ser Ser Thr
            20                  25                  30

Leu Lys Gly Val Thr Val Pro Glu Asp Arg A la Pro Ser Met Ile Asp
        35                  40                  45

Glu Tyr Pro Ile Leu Ala Val Ala Ala Ala P he Ala Glu Gly Ala Thr
    50                  55                  60

Val Met Asn Gly Leu Glu Glu Leu Arg Val L ys Glu Ser Asp Arg Leu
65                  70                  75                  80

Ser Ala Val Ala Asn Gly Leu Lys Leu Asn G ly Val Asp Cys Asp Glu
                85                  90                  95

Gly Glu Thr Ser Leu Val Val Arg Gly Arg P ro Asp Gly Lys Gly Leu

```
                    100              105              110
Gly Asn Ala Ser Gly Ala Ala Val Ala Thr H is Leu Asp His Arg Ile
            115              120              125

Ala Met Ser Phe Leu Val Met Gly Leu Val S er Glu Asn Pro Val Thr
    130              135              140

Val Asp Asp Ala Thr Met Ile Ala Thr Ser P he Pro Glu Phe Met Asp
145              150              155              160

Leu Met Ala Gly Leu Gly Ala Lys Ile Glu L eu Ser Asp Thr Lys Ala
                165              170              175

Ala

<210> SEQ ID NO 16
<211> LENGTH: 45
<212> TYPE: DNA
<213> ORGANISM: Artificial
<220> FEATURE:
<223> OTHER INFORMATION: Synthetic

<400> SEQUENCE: 16
aggctgcttg atgagctcgg tacccgggga tccatggagc cgaat            45

<210> SEQ ID NO 17
<211> LENGTH: 18
<212> TYPE: DNA
<213> ORGANISM: Artificial
<220> FEATURE:
<223> OTHER INFORMATION: Linker

<400> SEQUENCE: 17
aattaggggc atgcccct                                           18

<210> SEQ ID NO 18
<211> LENGTH: 24
<212> TYPE: DNA
<213> ORGANISM: Artificial
<220> FEATURE:
<223> OTHER INFORMATION: linker

<400> SEQUENCE: 18
gccactcgag ctaggtaccc tgca                                    24

<210> SEQ ID NO 19
<211> LENGTH: 22
<212> TYPE: DNA
<213> ORGANISM: Artificial
<220> FEATURE:
<223> OTHER INFORMATION: Linker

<400> SEQUENCE: 19
aattcatttg cggccgcaaa tg                                      22

<210> SEQ ID NO 20
<211> LENGTH: 22
<212> TYPE: DNA
<213> ORGANISM: Artificial
<220> FEATURE:
<223> OTHER INFORMATION: Linker

<400> SEQUENCE: 20
catttgcggc cgcaaatggt ac                                      22

<210> SEQ ID NO 21
<211> LENGTH: 20
```

```
<212> TYPE: DNA
<213> ORGANISM: Artificial
<220> FEATURE:
<223> OTHER INFORMATION: Linker

<400> SEQUENCE: 21
agcttgcagc ggccgctgca                                              20

<210> SEQ ID NO 22
<211> LENGTH: 20
<212> TYPE: DNA
<213> ORGANISM: Artificial
<220> FEATURE:
<223> OTHER INFORMATION: Linker

<400> SEQUENCE: 22
agctcgcagc ggccgctgca                                              20

<210> SEQ ID NO 23
<211> LENGTH: 20
<212> TYPE: DNA
<213> ORGANISM: Artificial
<220> FEATURE:
<223> OTHER INFORMATION: Linker

<400> SEQUENCE: 23
gcgtcgccgg cgacgttcga                                              20

<210> SEQ ID NO 24
<211> LENGTH: 20
<212> TYPE: DNA
<213> ORGANISM: Artificial
<220> FEATURE:
<223> OTHER INFORMATION: Linker

<400> SEQUENCE: 24
cgatgcagcc atggctgcat                                              20

<210> SEQ ID NO 25
<211> LENGTH: 28
<212> TYPE: DNA
<213> ORGANISM: Artificial
<220> FEATURE:
<223> OTHER INFORMATION: Oligonucleotide

<400> SEQUENCE: 25
ctcgagtatt tttacaacaa ttaccaac                                     28

<210> SEQ ID NO 26
<211> LENGTH: 22
<212> TYPE: DNA
<213> ORGANISM: Artificial
<220> FEATURE:
<223> OTHER INFORMATION: Oligonucleotide

<400> SEQUENCE: 26
aatcaaggta accttgaatc ca                                           22

<210> SEQ ID NO 27
<211> LENGTH: 26
<212> TYPE: DNA
<213> ORGANISM: Artificial
<220> FEATURE:
<223> OTHER INFORMATION: Oligonucleotide

<400> SEQUENCE: 27
```
accaccaacg gtgttcttgc tgttga         26

<210> SEQ ID NO 28
<211> LENGTH: 27
<212> TYPE: DNA
<213> ORGANISM: Artificial
<220> FEATURE:
<223> OTHER INFORMATION: Oligonucleotide

<400> SEQUENCE: 28
gcattacatg ttaattatta catgctt         27

<210> SEQ ID NO 29
<211> LENGTH: 28
<212> TYPE: DNA
<213> ORGANISM: Artificial
<220> FEATURE:
<223> OTHER INFORMATION: Oligonucleotide

<400> SEQUENCE: 29
gtgatacgag tttcaccgct agcgagac         28

<210> SEQ ID NO 30
<211> LENGTH: 24
<212> TYPE: DNA
<213> ORGANISM: Artificial
<220> FEATURE:
<223> OTHER INFORMATION: Oligonucleotide

<400> SEQUENCE: 30
taccttgcgt ggaccaaaga ctcc         24

<210> SEQ ID NO 31
<211> LENGTH: 19
<212> TYPE: DNA
<213> ORGANISM: Artificial
<220> FEATURE:
<223> OTHER INFORMATION: Oligonucleotide

<400> SEQUENCE: 31
gtcaacatgg tggagcacg         19

<210> SEQ ID NO 32
<211> LENGTH: 27
<212> TYPE: DNA
<213> ORGANISM: Artificial
<220> FEATURE:
<223> OTHER INFORMATION: Oligonucleotide

<400> SEQUENCE: 32
gtgagagttt atgactggag gcgcatc         27

<210> SEQ ID NO 33
<211> LENGTH: 24
<212> TYPE: DNA
<213> ORGANISM: Artificial
<220> FEATURE:
<223> OTHER INFORMATION: Oligonucleotide

<400> SEQUENCE: 33
gtccgcacgg agagccacaa acga         24